United States Patent
Yao

(10) Patent No.: US 10,336,704 B2
(45) Date of Patent: Jul. 2, 2019

(54) METHOD FOR PREPARING INDENOISOQUINOLINE DERIVATIVES

(71) Applicant: NATIONAL TAIWAN NORMAL UNIVERSITY, Taipei (TW)

(72) Inventor: Ching-Fa Yao, Taipei (TW)

(73) Assignee: NATIONAL TAIWAN NORMAL UNIVERSITY, Taipei (TW)

( * ) Notice: Subject to any disclaimer, the term of this patent is extended or adjusted under 35 U.S.C. 154(b) by 0 days.

(21) Appl. No.: 15/857,701

(22) Filed: Dec. 29, 2017

(65) Prior Publication Data

US 2019/0127330 A1 May 2, 2019

(30) Foreign Application Priority Data

Nov. 1, 2017 (TW) .............................. 106137758 A

(51) Int. Cl.
*C07D 221/18* (2006.01)
*C07D 491/056* (2006.01)
*C07D 495/04* (2006.01)
*C07D 471/04* (2006.01)

(52) U.S. Cl.
CPC ......... *C07D 221/18* (2013.01); *C07D 471/04* (2013.01); *C07D 491/056* (2013.01); *C07D 495/04* (2013.01)

(58) Field of Classification Search
CPC .......................... C07D 221/18; C07D 491/056
See application file for complete search history.

(56) References Cited

U.S. PATENT DOCUMENTS 5,554,620 A 9/1996 DeHaven-Hudkins et al.

FOREIGN PATENT DOCUMENTS

| EP | 1621529 A | 2/2006 |
|---|---|---|
| WO | 2004048322 A | 6/2004 |
| WO | 2015035223 A | 3/2015 |

OTHER PUBLICATIONS

Chia-Yu Huang, Veerababurao Kavala, Chun-Wei Kuo, Ashok Konala, Tang-Hao Yang, and Ching-Fa Yao, Synthesis of Biologically Active Indenoisoquinoline Derivatives via a One-Pot Copper(II)-Catalyzed Tandem Reaction, J.Org. Chem. 2017, 82, 1961-1968.
Glenda Kohlhagen, Kenneth D. Paull, Mark Cushman, Pamela Nagafuji, and Yves Pommier, Protein-Linked DNA Strand Breaks Induced by NSC 314622, a Novel Noncamptothecin Topoisomerase I Poison, Molecular Pharmacology, 54:50-58 (1998).
Mark Cushman, Muthusamy Jayaraman, Jeffrey A. Vroman,Anna K Fukunaga,Brian M. Fox, Glenda Kohlhagen,Dirk Strumberg,and Yves Pommier, Synthesis of New Indeno[1,2-c]isoquinolines: Cytotoxic Non-CamptothecinTopoisomerase I Inhibitors, J. Med. Chem. 2000, 43, 3688-3698.
Rocio Garcia-Carbonero and Jeffrey G. Supko, Current Perspectives on the Clinical Experience, Pharmacology, and Continued Development of the Camptothecins, Clinical Cancer Research, vol. 8, 641-661, Mar. 2002.
Craig J. Thomas, Nicolas J. Rahier, Sidney M. Hecht, Camptothecin: current perspectives, Bioorganic & Medicinal Chemistry 12 (2004) 1585-1604.
Yang Xu and Chengtao Her, Inhibition of Topoisomerase (DNA) I (TOP1): DNA Damage Repair and Anticancer Therapy, Biomolecules 2015, 5, 1652-1670.
Katherine E. Peterson,Maris A. Cinelli, Andrew E. Morrell,Akhil Mehta, Thomas S. Dexheimer, Keli Agama, Smitha Antony,Yves Pommier, and Mark Cushman, Alcohol-, Diol-, and Carbohydrate-Substituted Indenoisoquinolines as Topoisomerase I Inhibitors: Investigating the Relationships Involving Stereochemistry, Hydrogen Bonding, and Biological Activity, J. Med. Chem. 2011, 54, 4937-4953.

(Continued)

Primary Examiner — Emily A Bernhardt
(74) Attorney, Agent, or Firm — Bacon & Thomas, PLLC

(57) ABSTRACT

A method for preparing indenoisoquinoline derivatives represented by the following formula (I) is disclosed, which comprises the following steps:

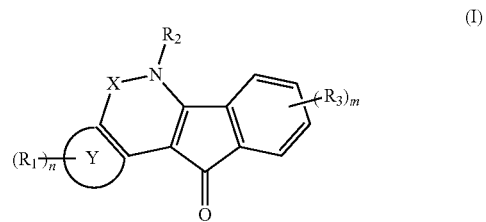

(A) providing a first reactant represented by the following formula (II) and a second reactant represented by the following formula (III):

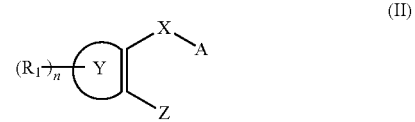

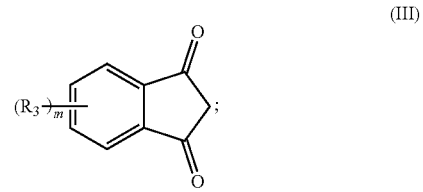

and (B) reacting the first reactant represented by the formula (II) and the second reactant represented by the formula (III) in a solvent and selectively adding $R_2NH_2$ therein, to obtain the indenoisoquinoline derivatives represented by the formula (I), wherein, $R_1$, $R_2$, $R_3$, A, X, Y, Z, m and n are defined in the specification.

14 Claims, No Drawings

(56) References Cited

OTHER PUBLICATIONS

Maris A. Cinelli, P. V. Narasimha Reddy, Peng-Cheng LV, Jian-Hua Liang, Lian Chen, Keli Agama, Yves Pommier,Richard B. Van Breemen, and Mark Cushman, Identification, Synthesis, and Biological Evaluation of Metabolites of the Experimental Cancer Treatment Drugs Indotecan (LMP400) and Indimitecan (LMP776) and Investigation of Isomerically Hydroxylated Indenoisoquinoline Analogues as Topoisomerase I Poisons, J. Med. Chem. 2012, 55, 10844-10862.

Daniel E. Beck, P. V. Narasimha Reddy, Wei LV, Monica Abdelmalak, Gabrielle S. Tender, Sophia Lopez, Keli Agama, Christophe Marchand, Yves Pommier, and Mark Cushman, Investigation of the Structure-Activity Relationships of Aza-A-RingIndenoisoquinoline Topoisomerase I Poisons, J. Med. Chem. 2016, 59, 3840-3853.

Mallesham Bejugam,Mekala Gunaratnam,Ebastian Muller, Deborah A. Sanders,Sven Sewitz, Jonathan A. Fletcher, Stephen Neidle, and Shankar Balasubramanian, Targeting the c-Kit Promoter G-quadruplexes with 6-Substituted Indenoisoquinolines, ACS Med. Chem. Lett. 2010, 1, 306-310.

Nathalie Wambang, Nadege Schifano-Faux, Alexandre Aillerie, Brigitte Baldeyrou, Camille Jacquet,Christine Bal-Mahieu, Till Bousquet, Sylvain Pellegrini, Peter T. Ndifon, Samuel Meignan,Ean-Fraçois Goossens, Amélie Lansiaux, Lydie Pélinski, Synthesis and biological activity of ferrocenyl indeno[1,2-c]isoquinolines as topoisomerase II inhibitors, Bioorganic & Medicinal Chemistry 24 (2016) 651-660.

Adina Ryckebusch,Deborah Garcin, Amelie Lansiaux,Jean-François Goossens,Brigitte Baldeyrou,Raymond Houssin,Christian Bailly,and Jean-Pierre Hénichart, Synthesis, Cytotoxicity, DNA Interaction, and Topoisomerase II Inhibition Properties of Novel Indeno[2,1-c]quinolin-7-one and Indeno[1,2-c] isoquinolin-5,11-dione Derivatives, J. Med. Chem. 2008, 51, 3617-3629.

Xiaoyun Zhang, Rubing Wang, Li Zhao, Na Lu, Jubo Wang, Qidong You, Zhiyu Li , Qinglong Guo, Synthesis and biological evaluations of novel indenoisoquinolines as topoisomerase I inhibitors, Bioorganic & Medicinal Chemistry Letters 22 (2012) 1276-1281.

Alison M. Suess, Mehmed Z. Ertem, Christopher J. Cramer, and Shannon S. Stahl, Divergence between Organometallic and Single-Electron-Transfer Mechanisms in Copper(II)-Mediated Aerobic C—H Oxidation,J. Am. Chem. Soc. 2013, 135, 9797-9804.

Nana Zhang, Binyao Li, Hongban Zhong and Jianhui Huang, Synthesis of N-alkyl and N-aryl isoquinolones and derivatives via Pd-catalysed C—H activation and cyclization reactions, Org. Biomol. Chem., 2012, 10, 9429.

Gyorgy Toth and Katalin E. Kover, Simple, Safe, Large Scale Synthesis of 5-Arylmethyl-2,2-Dimethyl-1,3-Dioxane-4,6-Dioanensd 3-Aryl-Propanoic Acids, Synthetic Communications, 25(19), 3067-3074 (1995).

J. D. Enas, J. G. Garcia, C. A. Mathis and J. M. Gerdes, Nucleophilic aromatic substitution reactions with the fluoride ion: formation of 5-fluoro-indanones and indandiones related to atipamezole, Journal of Fluorine Chemistry, 63 (1993) 233-241.

Palle V. R. Acharyulu, P. K. Dubey, P. V. V. Prasada Reddy,and Thatipally Suresh, Synthesis of Novel New 2-(2-(4-((3,4-Dihydro-4-oxo-3-aryl quinazolin-2-yl)methyl)piperazin-1-yl)acetoyloxy)-2-phenyl Acetic Acid Esters, Synthetic Communications1, 39: 3217-3231, 200.

Patrick Dallemagne, Sylvain Rault, Juan Carlos Pilo, Marie Paule Foloppe and Max Robba, One-Pot Cyclization of Alkoxy-3-Aminoindan-1-ones, Tetrahedron Letters, vol. 32, No. 44. pp. 6327-6328, 1991.

Howard E. Zimmerman and Marie-Laure Viriot-Villaume, Competitive Naphtho us. Benzo Bridging in the Di-r-methane Rearrangement of Benzo-2,3-naphthobarrelene. Exploratory and Mechanistic Organic Photochemistry. LXXIV, Journal of the American Chemical Society 95:4 1 Feb. 21, 1973.

Shih-Chia Tso,Mingliang Lou, Cheng-Yang Wu,Wen-Jun Gui, Jacinta L. Chuang, Lorraine K. Morlock, Noelle S. Williams, R. Max Wynn,Xiangbing Qi, and David T. Chuang, Development of Dihydroxyphenyl Sulfonylisoindoline Derivatives as Liver-Targeting Pyruvate Dehydrogenase Kinase Inhibitors, J. Med. Chem. 2017, 60, 1142-1150.

METHOD FOR PREPARING INDENOISOQUINOLINE DERIVATIVES

CROSS REFERENCE TO RELATED APPLICATION

This application claims the benefits of the Taiwan Patent Application Serial Number 106137758, filed on Nov. 1, 2017, the subject matter of which is incorporated herein by reference.

BACKGROUND

1. Field

The present disclosure relates to a method for preparing indenoisoquinoline derivatives and, more particularly, to a method for preparing indenoisoquinoline derivatives with a simple process (even only comprising one step).

2. Description of Related Art

Indeno[1,2-c]isoquinoline derivatives have been reported to have potential inhibition activities against topoisomerase I. In fact, camptothecin (CPT) derivatives appear to be best topoisomerase I (Top1) inhibitors that are currently available. However, extensive research by Cushman and coworkers revealed that indenoisoquinoline derivatives are novel Top1 inhibitors with better pharmacokinetic features than CPT and that they have good chemical stability and resistance to reversal after the drug is removed. In addition, indenoisoquinoline derivatives showed potential activity for treating visceral leishmaniasis. Indeno[1,2-c]isoquinoline derivatives such as LMP-400 and LMP-776 have also been used as multi-tumor treatment drugs. Some important indenoisoquinoline derivatives have structures shown as follows.

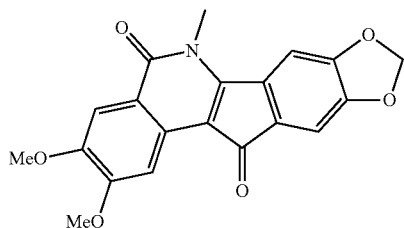

NSC 314622

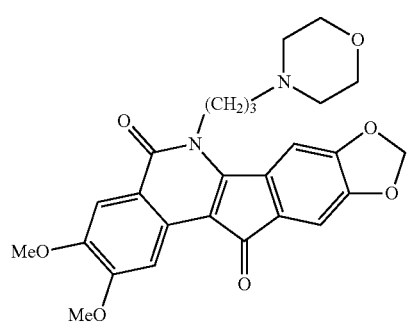

LMP-400

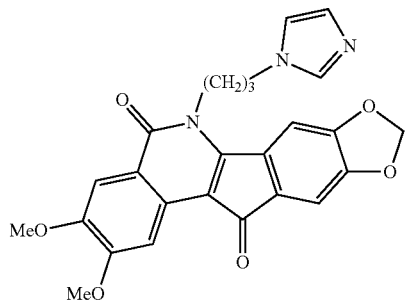

LMP-776

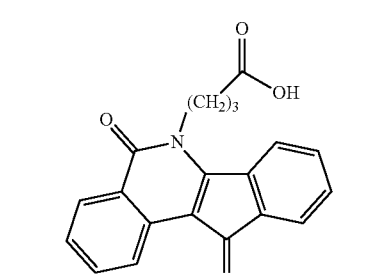

MJ238

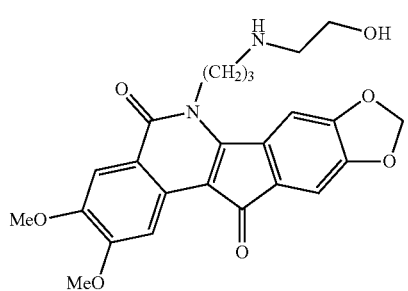

MJ-III-65

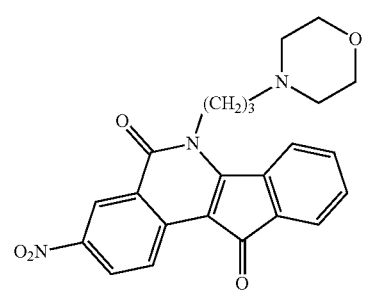

AM13-55

Nowadays, many methods have been reported to synthesize indenoisoquinoline derivatives. For example, indenoisoquinoline derivatives can be prepared by the condensation of indeno[1,2-c]isochromene-5,11-diones and amines, phthalic anhydrides and arylmethanimines, and bromomethyl benzonitrile and homophthalic anhydrides. Benzamide and benzonitrile are starting materials to obtain indenoisoquinoline derivatives after coupling reaction. Benzamide derivatives are used to obtain indenoisoquinoline derivatives by Grubbs reaction and photocatalytic reaction. Or, terminal alkynes and arylmethylidene undergoes cycloaddition reaction with Co catalyst, followed by oxidization with $SeO_2$ to obtain indenoisoquinoline derivatives.

However, most of the reported methods have one or more shortcomings such as the need for multiple steps, limited substrate scope, un-available starting materials and other stereochemistry problems. Therefore, it is desirable to provide a method for preparing indenoisoquinoline derivatives with a simple process (even only comprising one step), which can bring great benefits to the syntheses of clinical used indenoisoquinoline derivatives.

SUMMARY

The present disclosure is to provide a method for preparing indenoisoquinoline derivatives, wherein the indenoisoquinoline derivatives can be rapidly synthesized with a simple process by using the method of the present disclosure.

The present disclosure provides a method for preparing indenoisoquinoline derivatives represented by the following formula (I), which comprises the following steps:

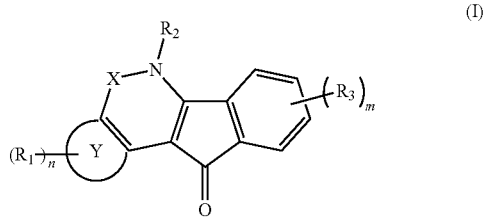

(A) providing a first reactant represented by the following formula (II) and a second reactant represented by the following formula (III):

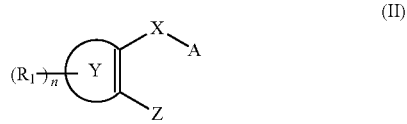

wherein A is —OH or —NHR$_2$;
X is —CO—, —SO$_2$—, —CS—, —SO—, or substituted or unsubstituted C$_{1-12}$ alkylene;
Y ring is substituted or unsubstituted C$_{6-14}$ aryl, or substituted or unsubstituted C$_{4-18}$ heteroaryl;
Z is F, Cl, Br or I;
n is an integral of 1 to 4;
each R$_1$ independently is H, nitro, halogen, or substituted or unsubstituted C$_{1-12}$ alkoxy; or when n is 2, two adjacent R$_1$ and carbon atoms attached thereto together form a substituted or unsubstituted C$_{3-18}$ alkylene oxide; and
R$_2$ is H, substituted or unsubstituted C$_{1-12}$ alkyl, substituted or unsubstituted C$_{2-12}$ alkenyl, substituted or unsubstituted C$_{3-18}$ cycloalkyl, substituted or unsubstituted C$_{3-18}$ cycloalkenyl, substituted or unsubstituted C$_{4-18}$ heterocycloalkyl, substituted or unsubstituted C$_{6-14}$ aryl, or substituted or unsubstituted C$_{4-18}$ heteroaryl,

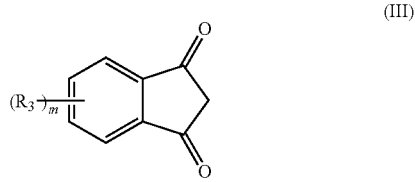

wherein m is an integral of 1 to 4; and
each R$_3$ independently is H, halogen, nitro, substituted or unsubstituted C$_{1-12}$ alkoxy; or when m is 2, two adjacent R$_3$ and carbon atoms attached thereto together form a substituted or unsubstituted C$_{3-18}$ alkylene oxide; and (B) reacting the first reactant represented by the formula (II) and the second reactant represented by the formula (III) in a solvent and selectively adding R$_2$NH$_2$ therein, to obtain the indenoisoquinoline derivatives represented by the formula (I).

Although various methods for preparing indenoisoquinoline derivatives have been reported, most of the reported methods have one or more shortcomings such as the need for multiple steps, limited substrate scope, un-available starting materials and other stereochemistry problems. In the method of the present disclosure, iodobenzene derivatives comprising lactam (X=—CO—), sulphonamide (X=—SO$_2$—), thioamide (X=CS), sulfinamide (X=SO) or alkylamine (X=alkyl) are used as a starting material, and reacted with indandione derivatives to obtain indenoisoquinoline derivatives rapidly and effectively. In some aspects of the present disclosure, the indenoisoquinoline derivatives even can be obtained with single step. In addition, in the method of the present disclosure, almost all the iodobenzene derivatives and the indandione derivatives are commercially available, and the problem of un-available starting materials can be prevented.

In the method of the present disclosure, the used solvent can be water, MeCN, DMF, DMSO, dioxane, toluene, or a combination thereof. In one embodiment of the present disclosure, the solvent is water. In another embodiment of the present disclosure, the solvent is MeCN.

In the method of the present disclosure, a catalyst can be further added in the step (B), wherein the catalyst comprises Cu$^+$ or Cu$^{2+}$. The catalyst can be selected from the group consisting of CuI, CuSO$_4$, CuCl, CuCl$_2$, and a hydrate thereof, but the present disclosure is not limited thereto. In one embodiment of the present disclosure, the catalyst is CuCl$_2$. In another embodiment of the present disclosure, the catalyst is CuSO$_4$.

In the method of the present disclosure, an alkali may be further added in the step (B), wherein the alkali can be a salt which comprises an alkaline metal. The alkali can be selected from the group consisting of K$_2$CO$_3$, Na$_2$CO$_3$, Cs$_2$CO$_3$, LiOH, NaOH, KOH, CsOH, Li$_3$PO$_4$, Na$_3$PO$_4$, K$_3$PO$_4$ and Cs$_3$PO$_4$, but the present disclosure is not limited thereto. In one embodiment of the present disclosure, the alkali is Cs$_2$CO$_3$.

In one embodiment of the present disclosure, in the step (B), the used solvent is MeCO, the used catalyst is CuCl$_2$, and the used alkali is Cs$_2$CO$_3$. In another embodiment of the present disclosure, in the step (B), the used solvent is water, the used catalyst is CuCl$_2$, and the used alkali is Cs$_2$CO$_3$. However, the present disclosure is not limited thereto.

In the method of the present disclosure, the temperature in the step (B) is not particularly limited, and can be adjusted according to the used solvent and reactor. For example, the temperature can be ranged from 70° C. to 150° C., or from 80° C. to 130° C. The reactor used in the step (B) is also not particularly limited. For example, the reaction can be performed with heat at room temperature and atmosphere in an opening system, the reaction can be performed with heat by using a micro-reactor, or the reaction can be performed by using a high pressure system. However, the present disclosure is not limited thereto.

In the method of the present disclosure, X in the formulas (I) and (II) can be —CO—, —SO$_2$—, —CS—, —SO—, or substituted or unsubstituted C$_{1-12}$ alkylene. In one embodiment of the present disclosure, X is —CO— or —SO$_2$—.

In the method of the present disclosure, R$_2$ can be H, substituted or unsubstituted C$_{1-12}$ alkyl, substituted or unsubstituted C$_{2-12}$ alkenyl, substituted or unsubstituted C$_{3-18}$ cycloalkyl, substituted or unsubstituted C$_{3-18}$ cycloalkenyl, substituted or unsubstituted C$_{4-18}$ heterocycloalkyl, substituted or unsubstituted C$_{6-14}$ aryl, or substituted or unsubstituted C$_{4-18}$ heteroaryl. In one embodiment of the present disclosure, R$_2$ is H, methyl, ethyl, propyl, butyl, allyl, phenyl, benzyl, morpholinoethyl, morpholinopropyl, imidazolethyl, imidazolpropyl, methoxyethyl, methoxypropyl, methoxybutyl, phenylethyl, phenylpropyl, phenylbutyl, fluorophenyl, chlorophenyl,

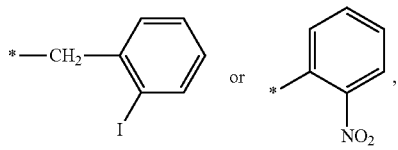

wherein * is a bonding position.

In the method of the present disclosure, Z in the formula (II) can be F, Cl, Br or I. In one embodiment of the present disclosure, Z is I.

In one embodiment of the present disclosure, the formula (II) can be one of the following formulas (II-1) to (II-3):

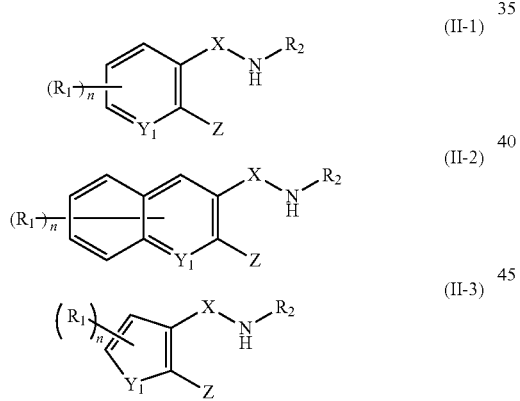

wherein Y$_1$ is C, N or S.

In one embodiment of the present disclosure, the formula (II) is one of the following formulas (II-4) to (II-8):

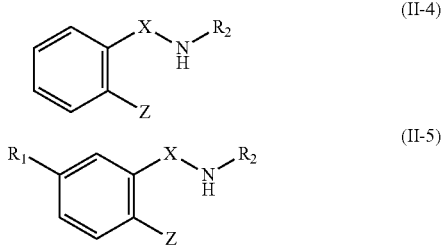

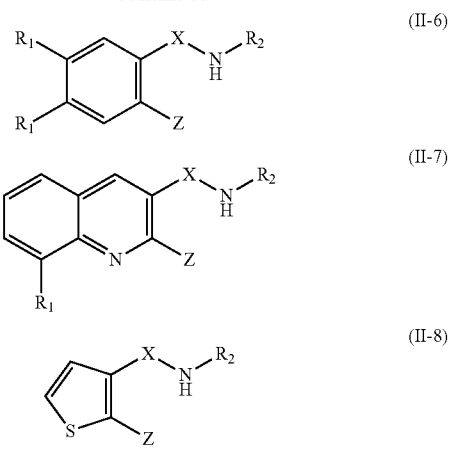

wherein, in the formulas (II-5) to (II-7), R$_1$ is nitro, Br, Cl, methoxy, ethoxy, propoxy or butoxy; or in the formula (II-6), two adjacent R$_1$ and carbon atoms attached thereto together form a dioxolane.

In one embodiment of the present disclosure, the formula (III) can be one of the following formulas (III-1) to (III-4):

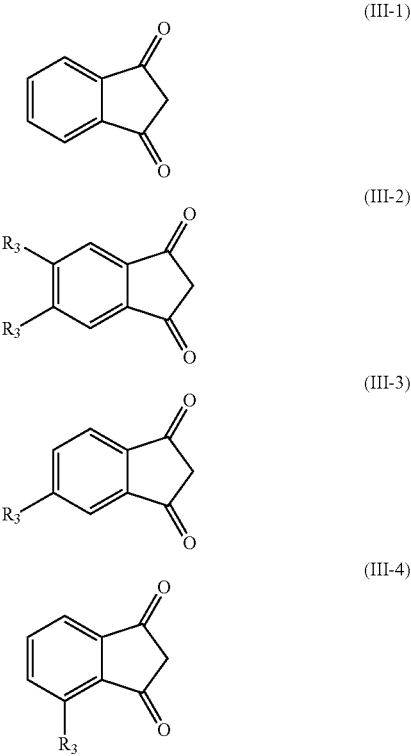

wherein, in the formulas (III-2) to (III-4), R$_3$ is Br, nitro, substituted or unsubstituted C$_{1-12}$ alkoxy; or in the formulas (III-2), two adjacent R$_3$ and carbon atoms attached thereto together form a substituted or unsubstituted C$_{3-18}$ alkylene oxide. In another embodiment of the present disclosure, in the formulas (III-2) to (III-4), R$_3$ is methoxy, ethoxy or propoxy; or in the formula (III-2), two adjacent R$_3$ and carbon atoms attached thereto together form dioxolane.

In one embodiment of the present disclosure, when A is —NHR$_2$, R$_2$NH$_2$ is not added into the reaction in the step (B).

In another embodiment of the present disclosure, when A is —OH, the step (B) may further comprise the following steps: (B1) reacting the first reactant represented by the formula (II) and the second reactant represented by the formula (III) in the solvent to obtain an intermediate represented by the following formula (IV):

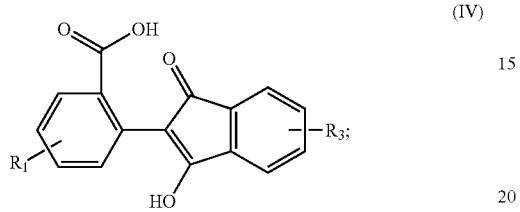

and (B2) reacting the intermediate represented by the formula (IV) with R$_2$NH$_2$ to obtain the indenoisoquinoline derivatives represented by the formula (I).

In the step (B1), a catalyst can be further added into the reaction, wherein the catalyst comprises Cu$^+$ or Cu$^{2+}$. The catalyst can be selected from the group consisting of CuI, CuSO$_4$, CuCl, CuCl$_2$, and a hydrate thereof, but the present disclosure is not limited thereto. In one embodiment of the present disclosure, the catalyst is CuCl$_2$. In another embodiment of the present disclosure, the catalyst is CuSO$_4$.

In addition, in the step (B1), an alkali is further added into the reaction, wherein the alkali can be a salt which comprises an alkaline metal. The alkali can be selected from the group consisting of K$_2$CO$_3$, Na$_2$CO$_3$, Cs$_2$CO$_3$, LiOH, NaOH, KOH, CsOH, Li$_3$PO$_4$, Na$_3$PO$_4$, K$_3$PO$_4$ and Cs$_3$PO$_4$, but the present disclosure is not limited thereto. In one embodiment of the present disclosure, the used alkali is Cs$_2$CO$_3$.

Furthermore, in the step (B2), an acid can be further added into the reaction. By the addition of the acid, the intermediate represented by the formula (IV) and R$_2$NH$_2$ can be reacted under an acidic environment. Herein, the pH in the step (B2) can be ranged from 1 to 5, or from 1 to 3. The used amount of the acid can be ranged from 3 equivalent to 5 equivalent. An example of the acid can be camphorsulfonic acid (CSA), but the present disclosure is not limited thereto.

In one embodiment of the present disclosure, the formula (I) can be one of the following formulas (I-1) to (I-9):

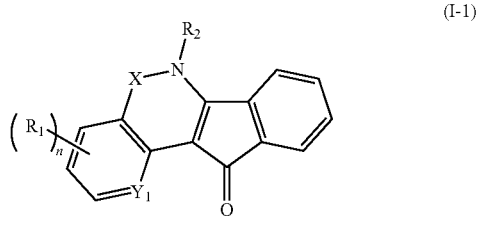

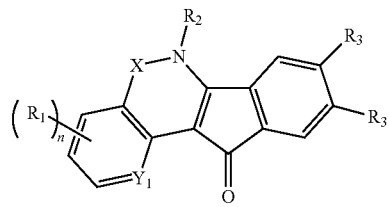

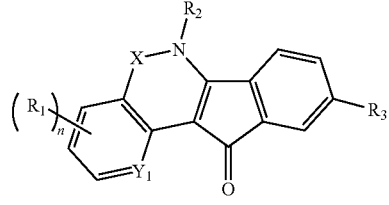

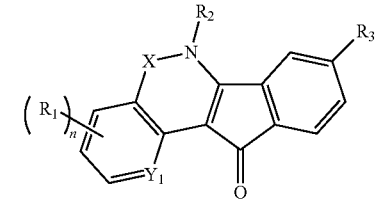

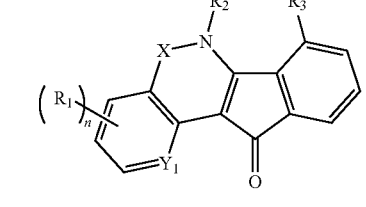

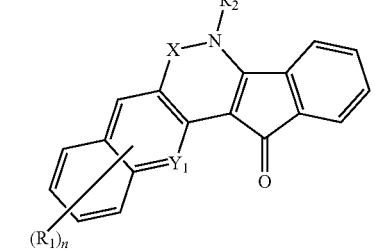

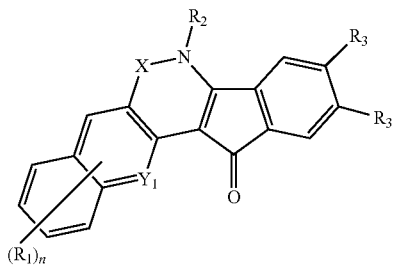

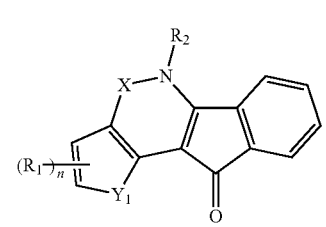

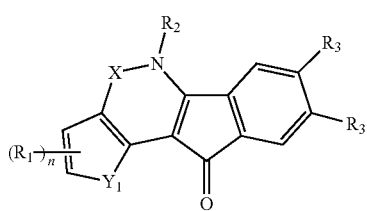

(I-9)

wherein $Y_1$ is C, N or S; and in the formulas (I-2) to (I-5), (I-7) and (I-9), $R_3$ is substituted or unsubstituted $C_{1-12}$ alkoxy; or in the formulas (I-2), (I-7) and (I-9), two adjacent $R_3$ and carbon atoms attached thereto together form a substituted or unsubstituted $C_{3-18}$ alkylene oxide.

In one embodiment of the present disclosure, the formula (I) can be one of the following formulas (I-10) to (I-20);

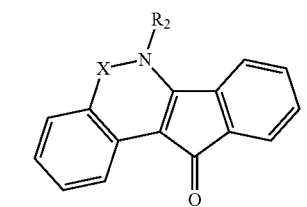

(I-10)

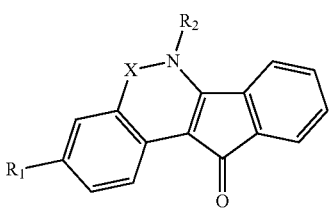

(I-11)

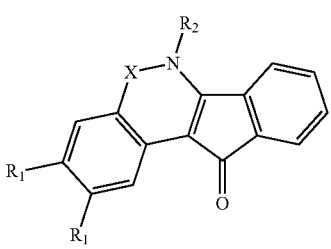

(I-12)

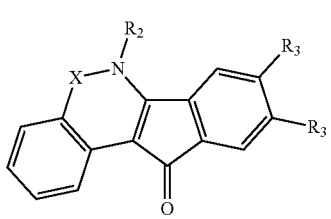

(I-13)

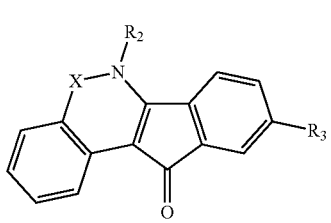

(I-14)

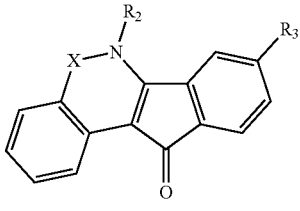

(I-15)

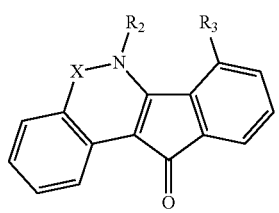

(I-16)

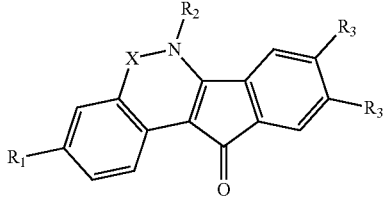

(I-17)

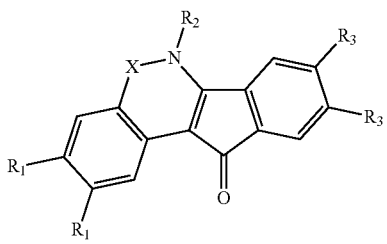

(I-18)

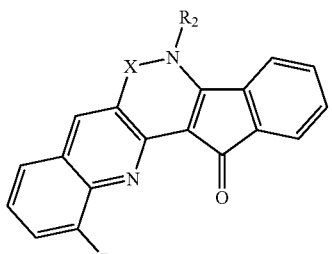

(I-19)

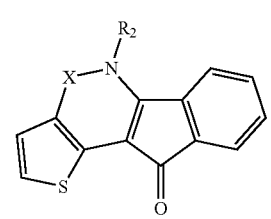

(I-20)

wherein, in the formulas (I-11), (I-12), (I-17), (I-18) and (I-19), $R_1$ is nitro, Br, Cl, methoxy, ethoxy, propoxy or butoxy; or in the formulas (I-12) and (I-18), two adjacent $R_1$ and carbon atoms attached thereto together form dioxolane; and in the formulas (I-13) to (I-18), $R_3$ is methoxy, ethoxy or propoxy; or in the formulas (I-13), (I-17) and (I-18), two adjacent $R_3$ and carbon atoms attached thereto together form dioxolane.

In one embodiment of the present disclosure, the formula (I) can be one of the following formulas (1) to (46):
(1)
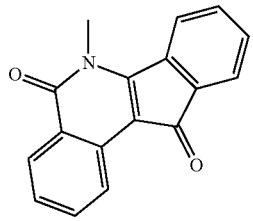
(2)
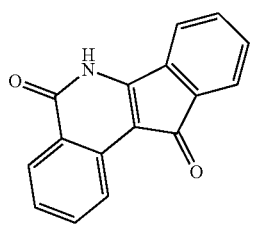
(3)
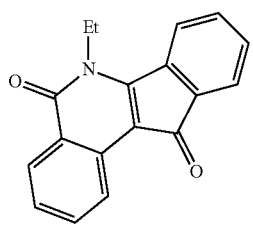
(4)
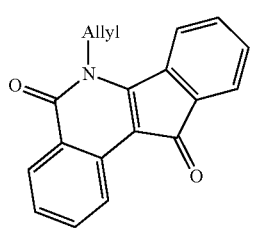
(5)
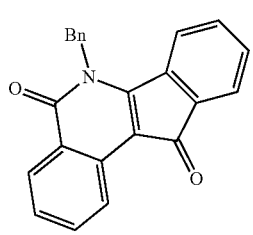
(6)
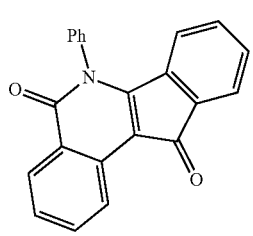
(7)
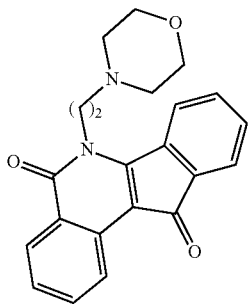
(8)
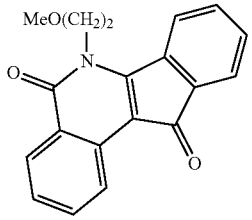
(9)
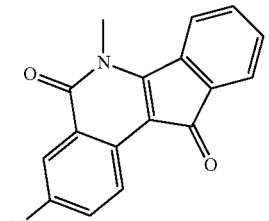
(10)
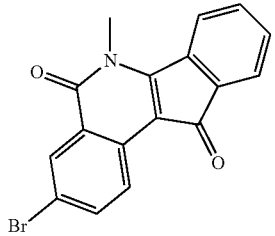
(11)
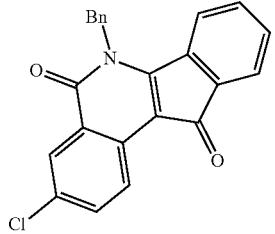
(12)
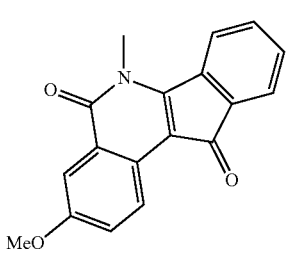

-continued
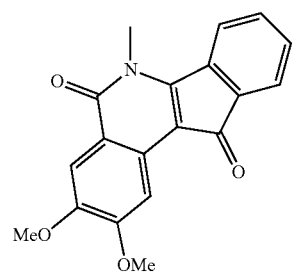
(13)
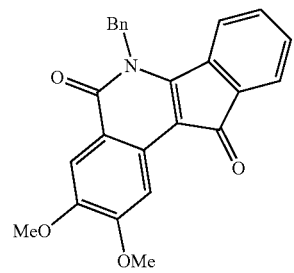
(14)
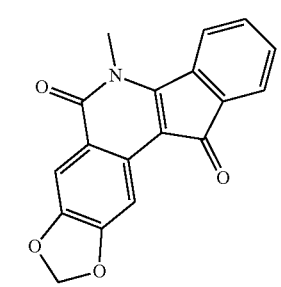
(15)
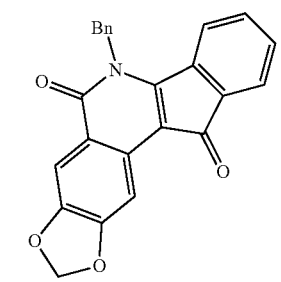
(16)
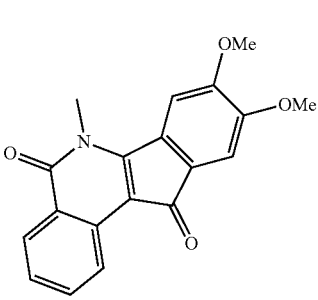
(17)
-continued
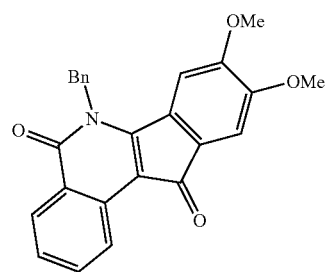
(18)
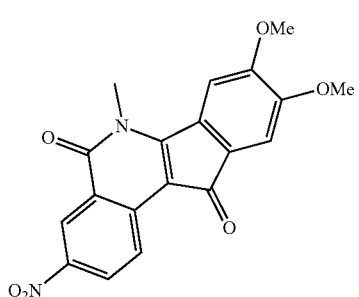
(19)
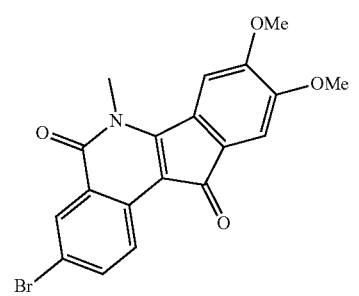
(20)
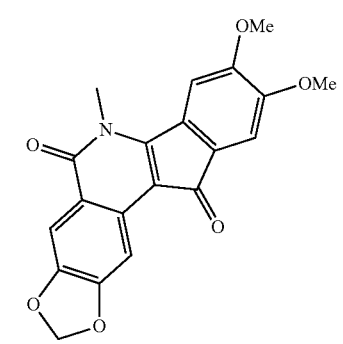
(21)
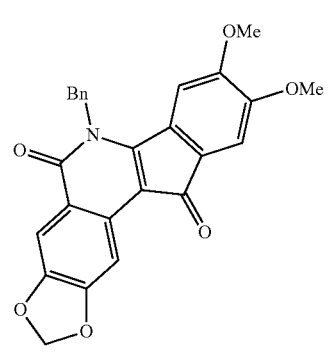
(22)

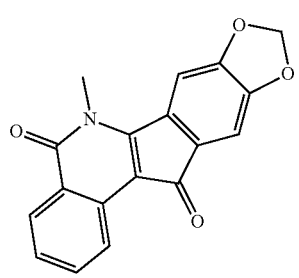
(23)
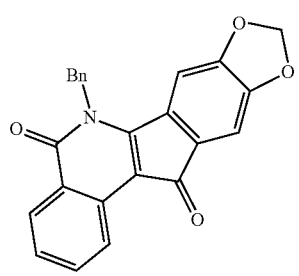
(24)
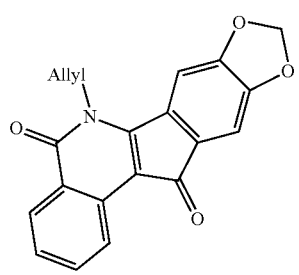
(25)
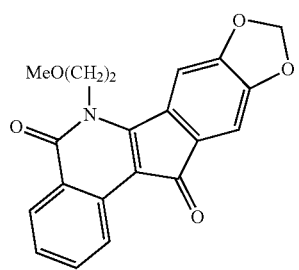
(26)
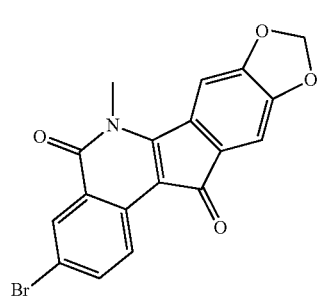
(27)
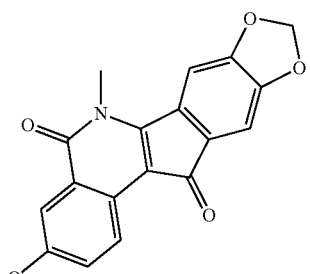
(28)
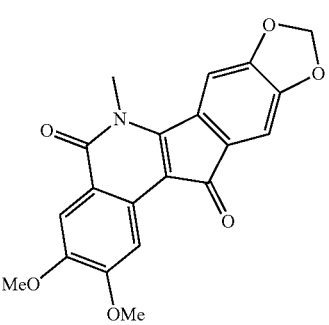
(29)
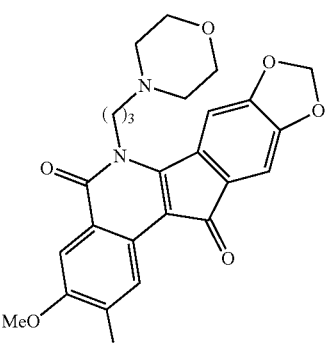
(30)
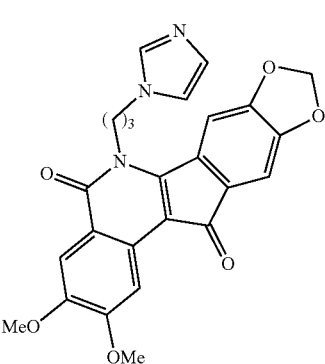
(31)
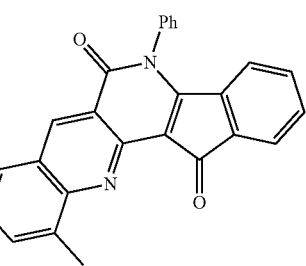
(32)

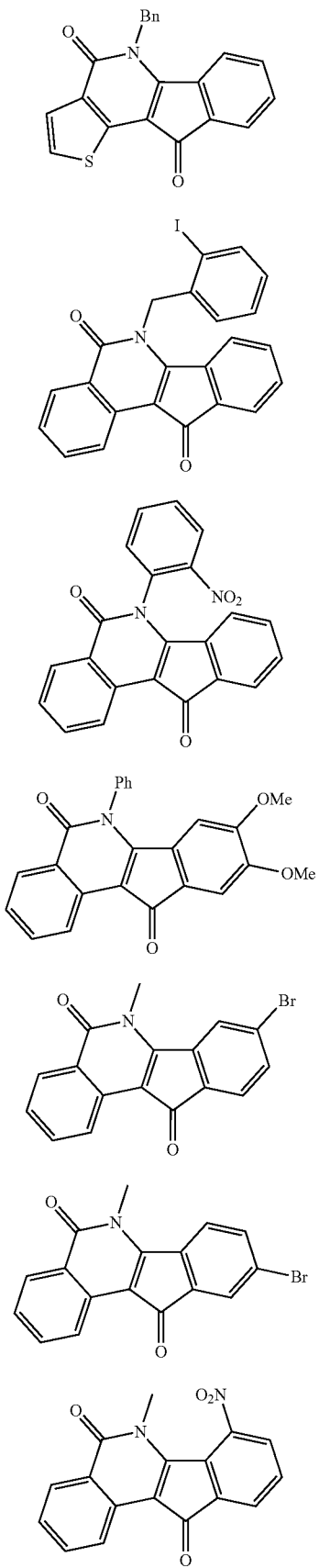
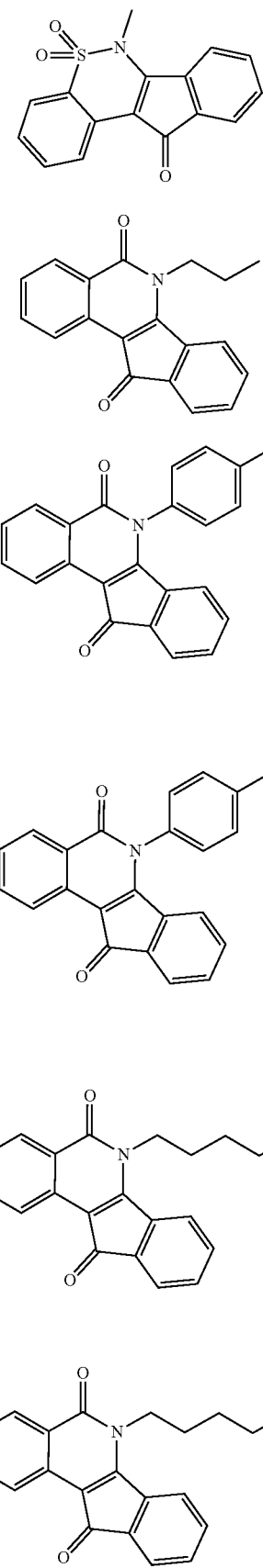

-continued

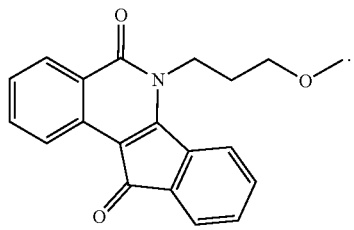

(46)

In the method of the present disclosure, alkyl(ene), alkoxy, alkenyl, cycloalkyl, cycloalkenyl, alkylene oxide, heterocycloalkyl, aryl, and heteroaryl present in the compounds include both substituted and unsubstituted moieties, unless specified otherwise. Possible substituents include, but are not limited to, alkyl, cycloalkyl, halogen, alkoxy, alkenyl, heterocycloalkyl, aryl, heteroaryl, ester, amino or carboxyl; but alkyl cannot be substituted with alkyl.

In the present disclosure, the term "halogen" includes F, Cl, Br and I.

In the present disclosure, the term "alkyl(ene)" refers to linear and branched alkyl, and includes, for example, linear or branched $C_{1-12}$ alkyl(ene), $C_{1-8}$ alkyl(ene) or $C_{1-6}$ alkyl(ene). Specific examples of alkyl(ene) include, but are not limited to, methyl(ene), ethyl(ene), n-propyl(ene), iso-propyl(ene), n-butyl(ene), sec-butyl(ene), iso-butyl(ene), tert-butyl(ene), pentyl(ene), neo-pentyl(ene) or hexyl(ene).

In the present disclosure, the term "alkoxy" refers to a moiety that the alkyl defined in the present disclosure coupled with an oxygen atom, and includes, for example, linear or branched $C_{1-12}$ alkoxy, $C_{1-8}$ alkoxy or $C_{1-6}$ alkoxy. Specific examples of alkoxy include, but are not limited to, methoxy, ethoxy, n-propoxy, iso-propoxy, n-butoxy, iso-butoxy, sec-butoxy, tert-butoxy, pentyloxy, neo-pentyloxy or hexyloxy.

In the present disclosure, the term "alkenyl" includes linear or branch hydrocarbon groups with at least one double bond, and includes, for example, linear or branch $C_{2-12}$ hydrocarbon groups with at least one double bond, linear or branch $C_{2-8}$ hydrocarbon groups with at least one double bond, or linear or branch $C_{2-6}$ hydrocarbon groups with at least one double bond. Examples of the alkenyl include, but are not limited to vinyl, propenyl or butenyl.

In the present disclosure, the term "cycloalkyl" includes cyclic saturated hydrocarbon groups, which includes, for example, 3 to 18 carbon atoms ($C_{3-18}$), 3 to 12 carbon atoms ($C_{3-12}$) or 3 to 8 carbon atoms ($C_{3-8}$). Examples of the cycloalkyl include, but are not limited to cyclopropyl, cyclobutyl, cyclopentyl, cyclohexyl, 1,4-cyclohexyl, cycloheptyl, cyclooctyl or adamantine.

In the present disclosure, the term "alkylene oxide" refers to a moiety that the cycloalkyl defined in the present disclosure coupled with at least one oxygen atom, and includes, for example, 3 to 18 carbon atoms ($C_{3-18}$), 3 to 12 carbon atoms ($C_{3-12}$) or 3 to 8 carbon atoms ($C_{3-8}$) as well as one or two oxygen atoms. Examples of the alkylene oxide include, but are not limited to, dioxolane.

In the present disclosure, the term "cycloalkenyl" includes cyclic unsaturated hydrocarbon groups, which includes 3 to 18 carbon atoms ($C_{3-18}$), 3 to 12 carbon atoms ($C_{3-12}$) or 3 to 8 carbon atoms ($C_{3-8}$). Examples of the cycloalkenyl include, but are not limited to cyclopentenyl, cyclohexenyl or cycloheptenyl.

In the present disclosure, the term "heterocycloalkyl" refers to a moiety that at least one carbon atom in the cycloalkyl defined in the present disclosure is substituted with at least one hetero atom, wherein each hetero atom is selected from O, S and N. Examples of the heterocycloalkyl include, but are not limited to tetrahydrofurfuryl.

In the present disclosure, the term "aryl" includes 6-membered single aromatic ring, 10-membered double aromatic ring or 14-membered triple aromatic ring. Examples of the aryl include, but are not limited to phenyl, naphthyl, pyrenyl, anthryl or phenanthryl.

In the present disclosure, the term "heteroaryl" refers to an aromatic ring having 5-8 membered single ring, 8-12 membered double ring or 11-14 membered triple ring and at least one hetero atom, in which each hetero atom in the ring is selected from O, S and N. Examples of the heteroaryl include, but are not limited to pyridyl, pyrimidinyl, furyl, thiazolyl, imidazolyl, or thienyl Other novel features of the disclosure will become more apparent from the following detailed description when taken in conjunction with the accompanying drawings.

DETAILED DESCRIPTION OF EMBODIMENT

The following embodiments when read with the accompanying drawings are made to clearly exhibit the above-mentioned and other technical contents, features and/or effects of the present disclosure. Through the exposition by means of the specific embodiments, people would further understand the technical means and effects the present disclosure adopts to achieve the above-indicated objectives. Moreover, as the contents disclosed herein should be readily understood and can be implemented by a person skilled in the art, all equivalent changes or modifications which do not depart from the concept of the present disclosure should be encompassed by the appended claims.

Analysis Instrument

NMR Spectroscopy $^1$H-NMR spectra were obtained with Bruker Avance 400 or Bruker Avance III HD 400 spectrometer system. The sample solvent was chloroform-$d^1$ (CDCl$_3$) or dimethylsulfoxide-$d^6$ (DMSO-$d_6$). Chemical shifts (δ) are reported in parts per million. For $^1$H-NMR spectrum, H absorption peak of the remaining chloroform in CDCl$_3$ is used as an internal standard, δ=7.26 ppm. The definition of the splitting pattern of the $^1$H-NMR spectrum is: s, singlet; d, doublet; t, triplet; q, quartet; quint, quintet; and m, multiplet. The coupling constant is presented by J in Hz. The data of the spectrum are sequentially illustrated by: chemical shift (splitting pattern, coupling constant and number of protons). $^{13}$C-NMR spectra were obtained with the same instruments, C absorption peak of the remaining chloroform in CDCl$_3$ is used as an internal standard, δ=77.23 ppm.

Thin Layer Chromatography (TLC)

The sample was spread with Merck silica gel 60 F$_{254}$ Al TLC plate, and observed the TLC plate with an UV light or a developer.

Column Chromatography

Merck Geduran® Si 60 (230-400 mesh) was used in the flash column chromatography, and samples were separated according to Still manual.

High Resolution Mass Spectrometry (HRMS)

Finnigan MAT 95S, Finnigan MAT-95XL or Finnigan/Thermo Quest MAT mass spectrometry was used, and the data are recorded by mass/charge (m/z).

Melting Point (mp)

Samples were placed in capillaries, and the melting points of the samples were measured with Mel-Temp melting point apparatus, which was not calibrated.

Reagents

Unless specified otherwise, reagents, solvents and drying agents used in the following experiments are purchased from Merck, TCI, Acros, Aldrich, Show or Lancaster without further purification. The D-containing solvent for NMR spectroscopy was purchased from Merck and Aldrich.

In addition, the eluent and the solvent, such as dichloromethane, chloroform, ethyl acetate, n-hexane and methanol, are ACS grade or obtained from purification by distillation using industrial grade solvent.

Most of the starting materials 2-iodobenzamide derivatives and 1,3-indandione derivatives are commercially available. In addition, 2-iodobenzamide derivatives were obtained from 2-iodobenzoic acid following publications ((a) A. M. Suess, M. Z. Ertem, C. J. Cramer, S. S. Stahl, *JACS* 2013, 135, 9797-9804. (b) N. Zhang, B. Li, H. Zhong, J. Huang, *Org. Biomol. Chem.* 2012, 10, 9429-9439.). Furthermore, 1,3-indandione derivatives were also obtained from benzaldehyde following publications ((a) Sterling Winthrop Inc., Patent: U.S. Pat. No. 5,554,620, A1, 1996. (b) G. Tóth, K. E. Kövér, *Synth. Commun.* 1995, 25, 3067-3074. (c) J. D. Enas, J. G. Garcia, C. A. Mathis, J. M. Gerdes, *J. Fluorine Chem.* 1993, 63, 233-241. 5,6-Methylenedioxyindandione 2c was prepared according to the following papers: (d) P. V. R. Acharyulu, P. K. Dubey, P. V. V. P. Reddy, T. Suresh, *Synth. Commun.* 2009, 39, 3217-3231. (e) Ube Industries, Ltd., Patent: EP1621529 A1, 2006. (f) Schering Corporation, Patent: WO200448322 A1, 2004. (g) P. Dallemagne, S. Rault, J. C. Pilo, M. P. Foloppe, M. Robba, *Tetrahedron Lett.* 1991, 32, 6327-6328. (h) H. E. Zimmerman, M.-L. Viriot-Villaume, *J. Am. Chem. Soc.* 1973, 95, 1274-1280. 5-bromoindandione 2d was prepared according to the following papers: (i) Tso, S.-C.; Lou, M.; Wu, C.-Y.; Gui, W.-J.; Cuang, J. L.; Morlock, L. K.; Williams, N. S.; Wynn, R. M.; Qi, X.; Chuang, D. T. *J. Med. Chem.* 2017, 60, 1142-1150. Peloton Therapeutics Inc., Patent: 201535223 A1, 2015.)

The process for preparing 2-iodobenzamide derivatives and 1,3-indandione derivatives are illustrated in the following Scheme I.

Scheme I

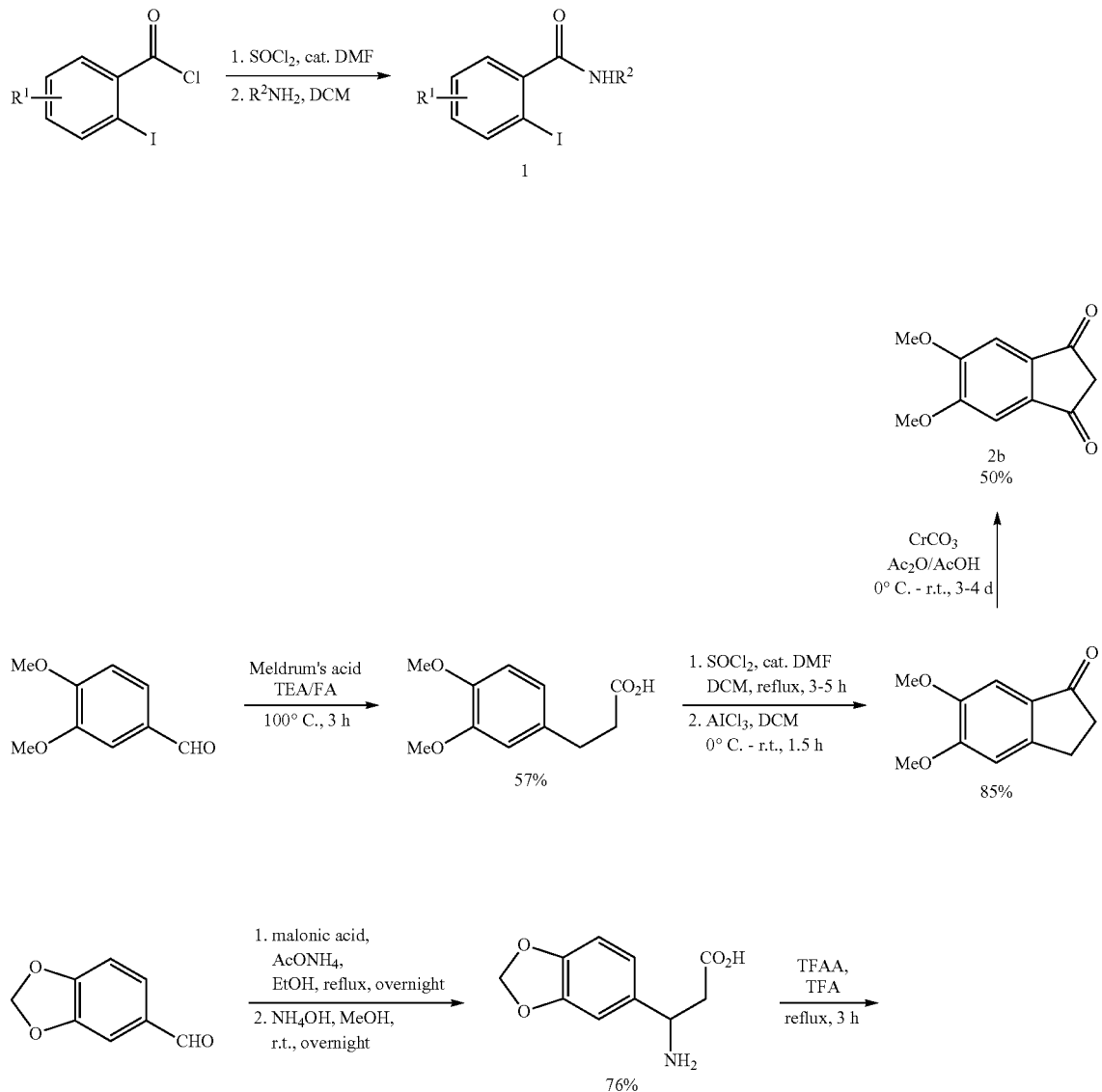

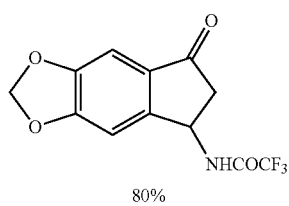 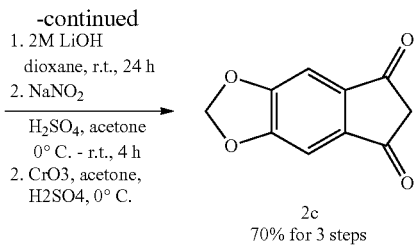

1. 2M LiOH
   dioxane, r.t., 24 h
2. NaNO₂
   H₂SO₄, acetone
   0° C. - r.t., 4 h
2. CrO3, acetone,
   H2SO4, 0° C.

80%

2c
70% for 3 steps

Embodiment 1

The process for preparing Compound (1) is illustrated in the following Scheme II.

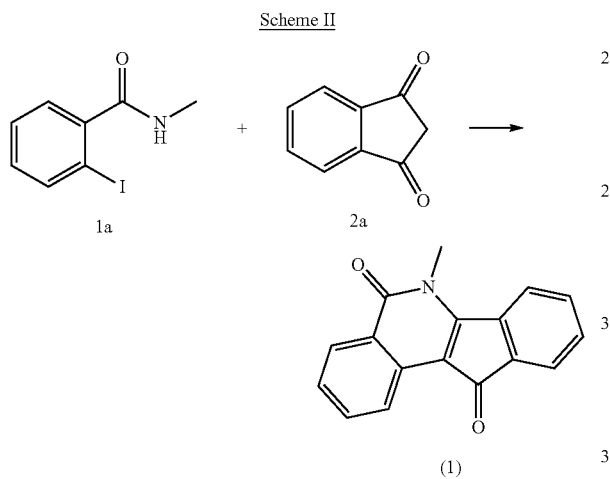

Scheme II (1)

Preparation with Organic Solvent

2-Iodobenzamide 1a (0.261 g, 1 mmol), 1,3-indandione 2a (0.219 g, 1.5 mmol) and $Cs_2CO_3$ (0.39 g, 1.2 mmol) were added to a 50 mL round bottom flask equipped with a magnetic stir bar and added 10-15 mL of acetonitrile. The mixture was heated to 90° C. for 5 min and then added $CuCl_2$ (0.0085 g, 0.05 mmol) and reacted for the time indicated. The progress of the reaction was monitored by TLC for disappearance of 2-Iodobenzamide 1a. After the reaction was completed, it was brought back to r.t. and added 1-2 mL of brine, the acetonitrile was removed under reduced pressure. More iced brine was added to solidify the product, the product was filtered by gravity filtration and then washed thoroughly with iced water to yield the pure Compound (1) (199 mg, 76%).

Preparation with Aqueous Solvent

2-Iodobenzamide 1a (0.261 g, 1 mmol), 1,3-indandione 2a (0.161 g, 1.1 mmol), $Cs_2CO_3$ (0.39 g, 1.2 mmol) and $CuSO_4 \cdot 5H_2O$ (1.25 mg, 5 µmol) were placed in 100 mL high pressure tube, and then 5 mL water was added therein, followed by sealing the tube. The reaction was heated and rapidly stirred in an oil bath, which is pre-heated to 130° C. The progress of the reaction was monitored by TLC. After the reaction was completed, it was brought back to r.t., and separated by a centrifugation. The product was washed with water. The centrifuge tube was placed in an oven to dry the product to yield the pure Compound (1) (214 mg, 82%).

Embodiments 2-31

The preparations of Compounds (2) to (31) were followed the preparation process using an organic solvent or an aqueous solvent of Embodiment 1. Herein, in the preparation process using the organic solvent, if the crude was sticky oil after removing acetonitrile, adding moderate amount of acetone or EA was acceptable to assist solidification of the product.

Embodiment 32

The process for preparing Compound (32) is illustrated in the following Scheme III. The process for preparing the indenoisoquinoline derivative with an organic solvent was similar to that illustrated in Embodiment 1, and is not repeated again.

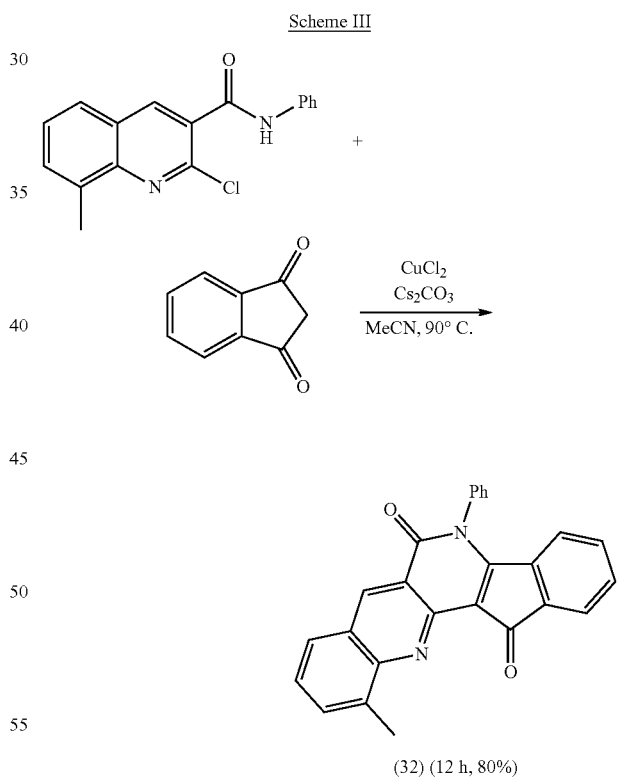

Scheme III

(32) (12 h, 80%)

Embodiment 33

The process for preparing Compound (33) is illustrated in the following Scheme IV. The process for preparing the indenoisoquinoline derivative with an organic solvent was similar to that illustrated in Embodiment 1, and is not repeated again.

Scheme IV

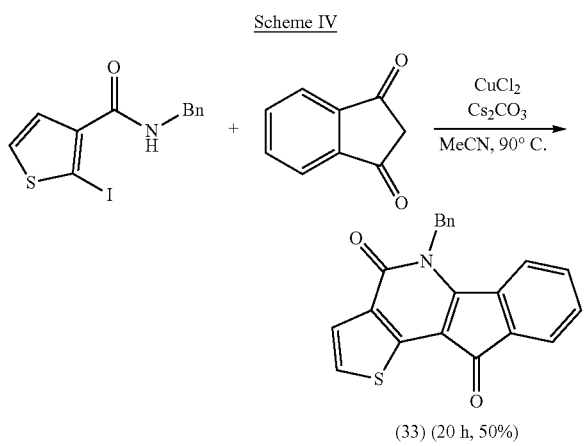

(33) (20 h, 50%)

Embodiment 34

The process for preparing Compound (34) is illustrated in the following Scheme V. The process for preparing the indenoisoquinoline derivative with an organic solvent was similar to that illustrated in Embodiment 1, and is not repeated again.

Scheme V

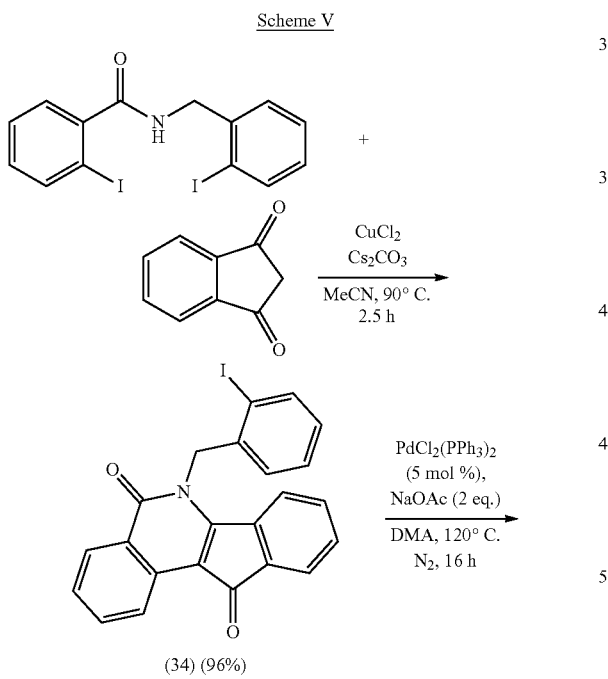

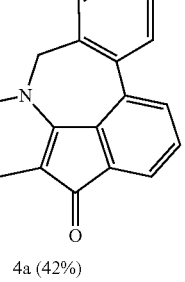

4a (42%)

Compound (34) was further proceeded with Heck reaction and reductive cyclization to obtain multi-ring compound (4a). Compound (34) (0.116 g, 0.25 mmol), $PdCl_2(PPh_3)_2$ (0.009 g, 0.0125 μmol) and NaOAc (0.041 g, 0.5 mmol) were added to a 10 mL round-bottom flask under $N_2$ atmosphere, then added 4 mL of DMA and heated to 120° C. for 16 h. After the reaction was completed, the mixture was purified by column chromatography using EA/Hexane as the eluent to yield the pure product (4a) as red solid (0.035 g, 42%).

Embodiment 35

The process for preparing Compound (35) is illustrated in the following Scheme VI. The process for preparing the indenoisoquinoline derivative with an organic solvent was similar to that illustrated in Embodiment 1, and is not repeated again.

Scheme VI

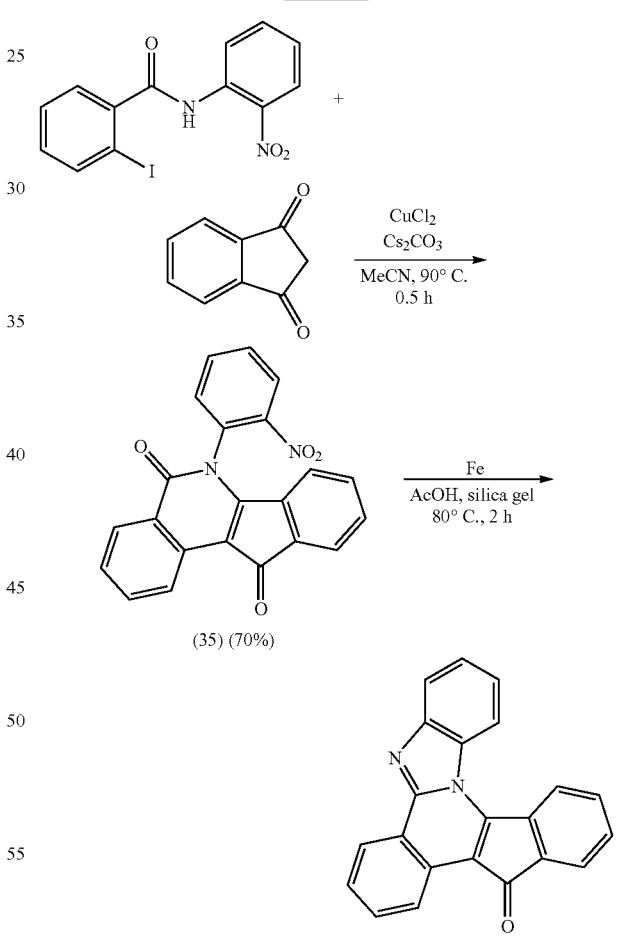

Compound (35) was further proceeded with Heck reaction and reductive cyclization to obtain multi-ring compound (5a). A mixture of Compound (35) (0.092 g, 0.25 mmol), Fe powder (0.07 g, 1.25 mmol) and AcOH (4 mL) were heated to 80° C. for 2 h. After the reaction was completed, the mixture was filtered through celite pad and wash with EA.

The eluent was evaporated and the solid collected was then washed with EA to yield the desired product (5a) as red solid (0.066 g, 83%).

Embodiments 36-39

The processes for preparing Compounds (36) to (39) were similar to the process for preparing the indenoisoquinoline derivative with an aqueous solvent illustrated in Embodiment 1, and is not repeated again.

Embodiment 40

The process for preparing Compound (40) is illustrated in the following Scheme VII.

Scheme VII

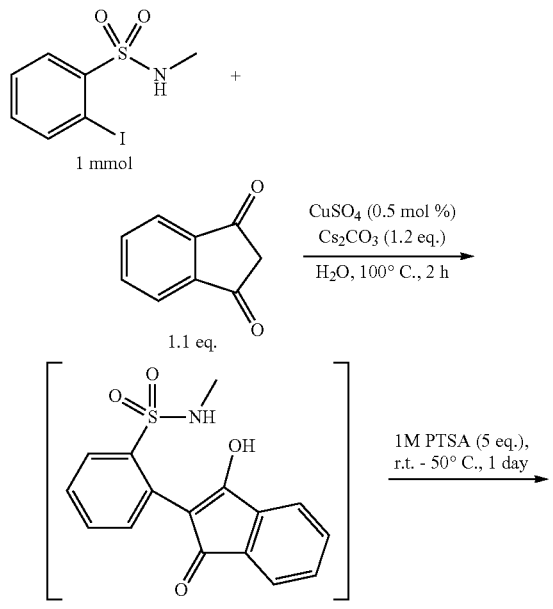

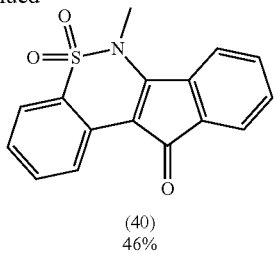

(40)
46%

N-methyl-2-iodobenzene sulfonamide (0.297 g, 1 mmol), 1,3-indandione (0.160 g, 1.1 mmol) and $Cs_2CO_3$ (0.391 g, 1.2 mmol) were placed in 50 mL high pressure tube, and then 4 mL water was added therein, followed by sealing the tube. The reaction was heated to 100° C. and reacted for 2 hr. After the reaction was brought back to r.t., 4 mL water was added to dilute the reaction. Under severe stirring, 1M p-toluene sulfonic acid aqueous solution (5 mL) was slowly added, slowly heated to 50° C. and reacted for 1 day. The progress of the reaction was monitored by TLC. After the reaction was completed, the product was separated by a centrifugation, and sequentially washed by water and saturated $NaHCO_3$ aqueous solution. The centrifuge tube was placed in an oven (60° C.) to dry the product to yield the pure Compound (40) (137 mg, 46%).

The names, reaction times (time), product weights (weight), yields, appearances (appear.) and melting points (mp.) of Compounds (1) to (40), (4a) and (5a) are listed in the following Tables 1 and 2. Table 1 shows the data in which the reaction was performed with an organic solvent, and Table 2 shows the data in which the reaction was performed with an aqueous solvent.

TABLE 1

| | | | Weight | Time | Yield | | Mp. |
|---|---|---|---|---|---|---|---|
| | Formula | Name | (mg) | (hr) | (%) | Appear. | (° C.) |
| (1) | | 6-methyl-5H-indeno[1,2-c]isoquinoline-5,11(6H)-dione | 199 | 3 | 76 | Red Solid | 240-242 |
| (2) | | 5H-indeno[1,2-c]isoquinoline-5,11(6H)-dione | 138 | 5 | 56 | Orange Solid | >350 |

Reaction using organic solvent

TABLE 1-continued

| | | | Reaction using organic solvent | | | | |
|---|---|---|---|---|---|---|---|
| | Formula | Name | Weight (mg) | Time (hr) | Yield (%) | Appear. | Mp. (° C.) |
| (3) | [structure with Et] | 5-ethyl-5H-indeno[1,2-c]isoquinoline-5,11(6H)-dione | 177 | 3 | 64 | Brown Solid | 184-186 |
| (4) | [structure with Allyl] | 6-allyl-5H-indeno[1,2-c]isoquinoline-5,11(6H)-dione | 187 | 8 | 65 | Red Solid | 160-162 |
| (5) | [structure with Bn] | 6-benzyl-5H-indeno[1,2-c]isoquinoline-5,11(6H)-dione | 202 | 3 | 61 | Orange Solid | 208-210 |
| (6) | [structure with Ph] | 6-phenyl-5H-indeno[1,2-c]isoquinoline-5,11(6H)-dione | 220 | 2.5 | 68 | Red Solid | 242-244 |
| (7) | [structure with morpholinoethyl] | 6-(2-morpholinoethyl)-5H-indeno[1,2-c]isoquinoline-5,11(6H)-dione | 224 | 2.5 | 62 | Pale brown Solid | 192-194 |
| (8) | [structure with MeO(CH$_2$)$_2$] | 6-(2-methoxyethyl)-5H-indeno[1,2-c]isoquinoline-5,11(6H)-dione | 199 | 2.5 | 65 | Red Solid | 184-186 |

TABLE 1-continued

| | | | Reaction using organic solvent | | | | |
|---|---|---|---|---|---|---|---|
| | Formula | Name | Weight (mg) | Time (hr) | Yield (%) | Appear. | Mp. (° C.) |
| (9) | | 6-methyl-3-nitro-5H-indeno[1,2-c]isoquinoline-5,11(6H)-dione | 261 | 1 | 85 | Red Solid | >350 |
| (10) | | 3-bromo-6-methyl-5H-indeno[1,2-c]isoquinoline-5,11(6H)-dione | 201 | 4 | 59 | Orange Solid | 272-274 |
| (11) | | 6-benzyl-3-chloro-5H-indeno[1,2-c]isoquinoline-5,11(6H)-dione | 249 | 6 | 67 | Orange Solid | 261-263 |
| (12) | | 3-methoxy-6-methyl-5H-indeno[1,2-c]isoquinoline-5,11(6H)-dione | 187 | 5 | 64 | Brown Solid | 228-230 |
| (13) | | 2,3-dimethoxy-6-methyl-5H-indeno[1,2-c]isoquinoline-5,11(6H)-dione | 171 | 6 | 53 | Red Solid | 281-283 |

TABLE 1-continued

| | | | Reaction using organic solvent | | | | |
|---|---|---|---|---|---|---|---|
| | Formula | Name | Weight (mg) | Time (hr) | Yield (%) | Appear. | Mp. (° C.) |
| (14) | 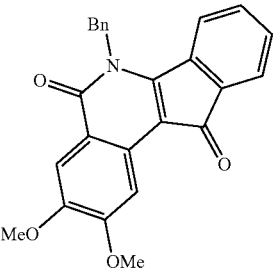 [SMILES: COc1cc2c3c(n(Cc4ccccc4)c(=O)c2cc1OC)-c1ccccc1C3=O] | 6-benzyl-2,3-dimethoxy-5H-indeno[1,2-c]isoquinoline-5,11(6H)-dione | 243 | 3 | 61 | Brown Solid | 289-290 |
| (15) | 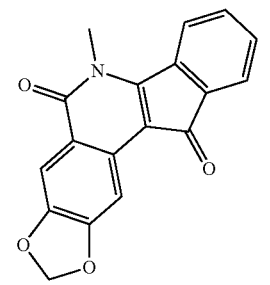 [SMILES: Cn1c2c(c3cc4c(cc3c1=O)OCO4)C(=O)c1ccccc1-2] | 6-methyl-5H-[1,3]dioxolo[4,5-g]indeno[1,2-c]isoquinoline-5,11(6H)-dione | 220 | 4 | 72 | Red Solid | 327-329 |
| (16) | 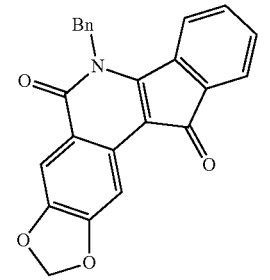 [SMILES: O=C1c2ccccc2-c2c1c1cc3c(cc1c(=O)n2Cc1ccccc1)OCO3] | 6-benzyl-5H-[1,3]dioxolo[4,5-g]indeno[1,2-c]isoquinoline-5,11(6H)-dione | 256 | 16 | 67 | Brown Solid | 302-304 |
| (17) | 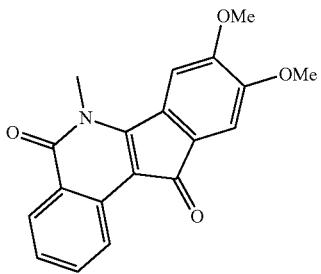 [SMILES: COc1cc2c(cc1OC)-c1c(c3ccccc3c(=O)n1C)C2=O] | 8,9-dimethoxy-6-methyl-5H-indeno[1,2-c]isoquinoline-5,11(6H)-dione | 206 | 3.5 | 64 | Brown Solid | 326-328 |
| (18) | 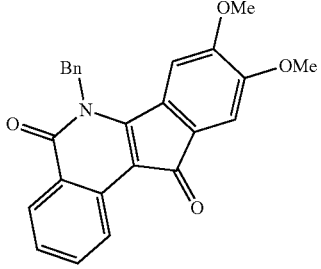 [SMILES: COc1cc2c(cc1OC)-c1c(c3ccccc3c(=O)n1Cc1ccccc1)C2=O] | 6-benzyl-8,9-dimethoxy-5H-indeno[1,2-c]isoquinoline-5,11(6H)-dione | 274 | 4.5 | 69 | Brown Solid | 272-274 |

TABLE 1-continued

Reaction using organic solvent

| | Formula | Name | Weight (mg) | Time (hr) | Yield (%) | Appear. | Mp. (° C.) |
|---|---|---|---|---|---|---|---|
| (19) | | 8,9-dimethoxy-6-methyl-3-nitro-5H-indeno[1,2-c]isoquinoline-5,11(6H)-dione | 268 | 1 | 73 | Brown Solid | 345-347 (D) |
| (20) | | 3-bromo-8,9-dimethoxy-6-methyl-5H-indeno[1,2-c]isoquinoline-5,11(6H)-dione | 251 | 2 | 63 | Brown Solid | >350 |
| (21) | | 8,9-dimethoxy-6-methyl-5H-[1,3]dioxolo[4,5-g]indeno[1,2-c]isoquinoline-5,11(6H)-dione | 223 | 4 | 61 | Brown Solid | 321-323 |
| (22) | | 6-benzyl-8,9-dimethoxy-5H-[1,3]dioxolo[4,5-g]indeno[1,2-c]isoquinoline-5,11(6H)-dione | 287 | 16 | 65 | Brown Solid | 315-317 |
| (23) | | 6-methyl-5H-[1,3]dioxolo[4',5':5,6]indeno[1,2-c]isoquinoline-5,1(6H)-dione | 202 | 3 | 66 | Brown Solid | 308-310 |

TABLE 1-continued

| | | | Weight (mg) | Time (hr) | Yield (%) | Appear. | Mp. (° C.) |
|---|---|---|---|---|---|---|---|
| | Formula | Name | | | | | |
| (24) | | 6-benzyl-5H-[1,3]dioxolo[4',5':5,6]indeno[1,2-c]isoquinoline-5,12(6H)-dione | 229 | 5 | 60 | Brown Solid | 297-299 |
| (25) | | 6-allyl-5H-[1,3]dioxolo[4',5':5,6]indeno[1,2-c]isoquinoline-5,12(6H)-dione | 249 | 4 | 75 | Brown Solid | 242-244 |
| (26) | | 6-(2-methoxyethyl)-5H-[1,3]dioxolo[4',5':5,6]indeno[1,2-c]isoquinoline-5,12(6H)-dione | 186 | 1.5 | 53 | Brown Solid | 205-207 (D) |
| (27) | | 3-bromo-6-methyl-5H-[1,3]dioxolo[4',5':5,6]indeno[1,2-c]isoquinoline-5,12(6H)-dione | 238 | 2.5 | 62 | Brown Solid | 322-324 (D) |
| (28) | | 3-methoxy-6-methyl-5H-[1,3]dioxolo[4',5':5,6]indeno[1,2-c]isoquinoline-5,12(6H)-dione | 218 | 5 | 65 | Brown Solid | 286-288 |

TABLE 1-continued

Reaction using organic solvent

| | Formula | Name | Weight (mg) | Time (hr) | Yield (%) | Appear. | Mp. (° C.) |
|---|---|---|---|---|---|---|---|
| (29) | | 2,3-dimethoxy-6-methyl-5H-[1,3]dioxolo[4',5':5,6]indeno[1,2-c]isoquinoline-5,12(6H)-dione | 201 | 10 | 55 | Brown Solid | 298-300 (D) |
| (30) | | 2,3-dimethoxy-6-(3-morpholinopropyl)-5H-[1,3]dioxolo[4',5':5,6]indeno[1,2-c]isoquinoline-5,12(6H)-dione | 259 | 18 | 54 | Brown Solid | 293-295 |
| (31) | | 6-(3-(1H-imidazol-1-yl)propyl)-2,3-dimethoxy-5H-[1,3]dioxolo[4',5':5,6]indeno[1,2-c]isoquinoline-5,12(6H)-dione | 225 | 18 | 49 | Brown Solid | 320-322 |
| (32) | | 11-methyl-5-phenyl-5H-benzo[b]indeno[1,2-h][1,6]naphthyridine-6,13-dione | 311 | 12 | 80 | Pale brown Solid | >350 |
| (33) | | 5-benzyl-4H-indeno[1,2-b]thieno[2,3-d]pyridine-4,10-(5H)-dione | 172 | 20 | 50 | Orange Solid | 232-234 |

TABLE 1-continued

| | | | Reaction using organic solvent | | | | |
|---|---|---|---|---|---|---|---|
| | Formula | Name | Weight (mg) | Time (hr) | Yield (%) | Appear. | Mp. (° C.) |
| (34) | | 6-(2-iodobenzyl)-5H-indeno[1,2-c]isoquinoline-5,11(6H)-dione | 445 | 2.5 | 96 | Orange Solid | 236-238 |
| (35) | | 6-(2-nitrophenyl)-5H-indeno[1,2-c]isoquinoline-5,11(6H)-dione | 258 | 0.5 | 70 | Pale brown Solid | 286-288 |
| (4a) | | 1H-6a-azabenzo-[a]benzo[5,6]cyclohepta[1,2,3,4-def]fluorene-1,6-(7H)-dione | 141 | — | 42 | Red Solid | 276-278 |
| (5a) | | 10H-benzo[4,5]imidazo[2,1-a]indeno[1,2-c]isoquinoline-10-one | 267 | — | 83 | Red Solid | 286-288 |

**(D): Decomposed

TABLE 2

| | Formula | Name | Weight (mg) | Time (hr) | Yield (%) | Appear. | Mp. (° C.) |
|---|---|---|---|---|---|---|---|
| | | Reaction using aqueous solvent | | | | | |
| (1) | | 6-methyl-5H-indeno[1,2-c]isoquinoline-5,11(6H)-dione | 219 | 1 | 84 | Red Solid | 240-244 |
| (2) | | 5H-indeno[1,2-c]isoquinoline-5,11(6H)-dione | 185 | 0.75 | 82 | Orange Solid | >350 |
| (4) | | 6-allyl-5H-indeno[1,2-c]isoquinoline-5,11(6H)-dione | 230 | 1 | 80 | Red Solid | 160-162 |
| (5) | | 6-benzyl-5H-indeno[1,2-c]isoquinoline-5,11(6H)-dione | 256 | 0.75 | 76 | Orange Solid | 208-210 |
| (6) | | 6-phenyl-5H-indeno[1,2-c]isoquinoline-5,11(6H)-dione | 268 | 0.7 | 83 | Red Solid | 242-244 |
| (9) | | 6-methyl-3-nitro-5H-indeno[1,2-c]isoquinoline-5,11(6H)-dione | 288 | 0.3 | 94 | Red Solid | >350 |

TABLE 2-continued

| | | | Reaction using aqueous solvent | | | | |
|---|---|---|---|---|---|---|---|
| | Formula | Name | Weight (mg) | Time (hr) | Yield (%) | Appear. | Mp. (° C.) |
| (10) | | 3-bromo-6-methyl-5H-indeno[1,2-c]isoquinoline-5,11(6H)-dione | 208 | 0.75 | 61 | Orange Solid | 272-274 |
| (12) | | 3-methoxy-6-methyl-5H-indeno[1,2-c]isoquinoline-5,11(6H)-dione | 224 | 1 | 77 | Brown Solid | 228-230 |
| (13) | | 2,3-dimethoxy-6-methyl-5H-indeno[1,2-c]isoquinoline-5,11(6H)-dione | 289 | 1 | 90 | Red Solid | 281-283 |
| (15) | | 6-methyl-5H-[1,3]dioxolo[4,5-g]indeno[1,2-c]isoquinoline-5,11(6H)-dione | 266 | 0.75 | 87 | Red Solid | 327-329 |
| (17) | | 8,9-dimethoxy-6-methyl-5H-indeno[1,2-c]isoquinoline-5,11(6H)-dione | 199 | 1 | 62 | Brown Solid | 326-328 |

TABLE 2-continued

Reaction using aqueous solvent

| | Formula | Name | Weight (mg) | Time (hr) | Yield (%) | Appear. | Mp. (° C.) |
|---|---|---|---|---|---|---|---|
| (20) | | 3-bromo-8,9-dimethoxy-6-methyl-5H-indeno[1,2-c]isoquinoline-5,11(6H)-dione | 288 | 0.75 | 72 | Brown Solid | >350 |
| (23) | | 6-methyl-5H-[1,3]dioxolo[4',5':5,6]indeno[1,2-c]isoquinoline-5,1(6H)-dione | 211 | 0.75 | 83 | Brown Solid | 308-310 |
| (26) | | 6-(2-methoxyethyl)-5H-[1,3]dioxolo[4',5':5,6]indeno[1,2-c]isoquinoline-5,12(6H)-dione | 234 | 0.5 | 67 | Brown Solid | 205-207 (D) |
| (28) | | 3-methoxy-6-methyl-5H-[1,3]dioxolo[4',5':5,6]indeno[1,2-c]isoquinoline-5,12(6H)-dione | 241 | 1 | 72 | Brown Solid | 286-288 |
| (30) | | 2,3-dimethoxy-6-(3-morpholinopropyl)-5H-[1,3]dioxolo[4',5':5,6]indeno[1,2-c]isoquinoline-5,12(6H)-dione | 244 | 2.5 | 51 | Brown Solid | 293-295 |

TABLE 2-continued

| | | | Reaction using aqueous solvent | | | | |
|---|---|---|---|---|---|---|---|
| | Formula | Name | Weight (mg) | Time (hr) | Yield (%) | Appear. | Mp. (° C.) |
| (31) | | 6-(3-(1H-imidazol-1-yl)propyl)-2,3-dimethoxy-5H-[1,3]dioxolo[4',5':5,6]indeno[1,2-c]isoquinoline-5,12(6H)-dione | 349 | 3 | 76 | Brown Solid | 320-322 |
| (36) | | 8,9-dimethoxy-6-phenyl-5H-indeno-[1,2-c]isoquinoline-5,11(6H)-dione | 318 | 0.75 | 83 | Brown Solid | 225-226 |
| (37) | | 8-bromo-6-methyl-5H-indeno-[1,2-c]isoquinoline-5,11(6H)-dione | 82 | 4 | 24 | Red Solid | 267-268 |
| (38) | | 9-bromo-6-methyl-5H-indeno-[1,2-c]isoquinoline-5,11(6H)-dione | 82 | 4 | 24 | Red Solid | 274-275 |
| (39) | | 6-methyl-7-nitro-5H-indeno-[1,2-c]isoquinoline-5,11(6H)-dione | 86 | 6 | 28 | Brown Solid | 289-290 |
| (40) | | 6-methylbenzo[e]indeno[1,2-c][1,2]thiazin-11(6H)-one 5,5-dioxide | 137 | — | 46 | Red Solid | 210-212 |

**(D): Decomposed

Embodiment 41

In the present embodiment, Compound (6) was prepared according to the following Scheme VIII.

Scheme VIII

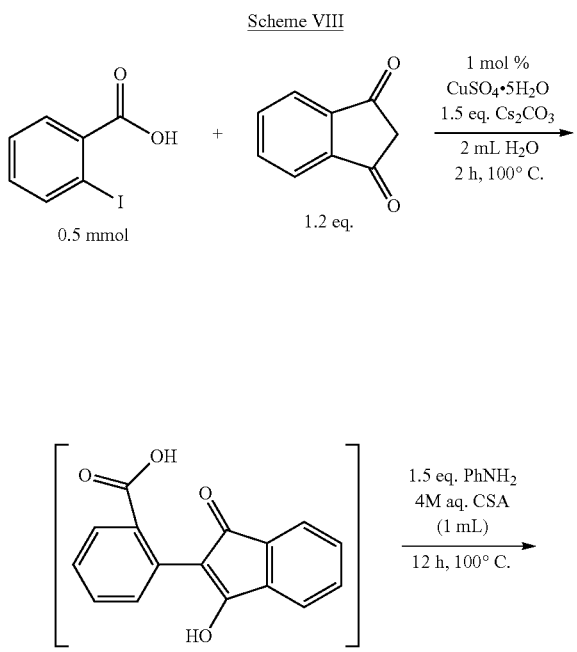

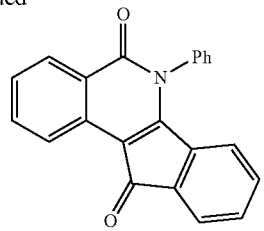

This reaction was an one-pot reaction. 2-iodobenzoic acid (0.5 mmol), 1,3-indandione (0.6 mmol), $CuSO_4 \cdot 5H_2O$ (1 mmol) and $Cs_2CO_3$ (0.75 mmol) were added into a reaction bottle, followed by adding water (2 mL). The reaction was performed at 100° C. for 2 hr, and an intermediate was obtained (83%). After the first step was completed, it was brought back to r.t. to proceed the second step. Then, aniline (1.5 eq.) was added into the reaction bottle, followed by slowly adding CSA aqueous solution (4 eq.). After the addition was completed, pH stripes were used to confirm whether the pH value of the reaction was reached to 1. Then, the reaction was heated to 100° C. After 12 hr, Compound (6) was obtained.

Embodiments 42-48

The preparations of Compounds (5), (26), (42) to (46) were similar to Scheme VIII shown in Embodiment 41, and only the amounts of the reactants and the reaction times were adjusted.

The names, reaction times (time), product weights (weight), yields, appearances (appear.) and melting points (mp.) of Compounds (5), (6), (26), (42) to (46) prepared in Embodiments 41 to 48 are listed in the following Table 3.

TABLE 3

| Formula | | Name | Weight (mg) | Time for 2$^{nd}$ step (hr) | Yield (%) | Appear. | Mp. (° C.) |
|---|---|---|---|---|---|---|---|
| (5) | Bn-substituted structure | 6-benzyl-5H-indeno[1,2-c]isoquinoline-5,11(6H)-dione | 256 | 12 | 70 | Orange Solid | 208-210 |
| (6) | Ph-substituted structure | 6-phenyl-5H-indeno[1,2-c]isoquinoline-5,11(6H)-dione | 268 | 12 | 90 | Red Solid | 242-244 |

TABLE 3-continued

| | Formula | Name | Weight (mg) | Time for 2nd step (hr) | Yield (%) | Appear. | Mp. (° C.) |
|---|---|---|---|---|---|---|---|
| (26) | MeO(CH₂)₂ structure | 6-(2-methoxyethyl)-5H-[1,3]dioxolo[4',5':5,6]indeno[1,2-c]isoquinoline-5,12(6H)-dione | 186 | 12 | 60 | Brown Solid | 205-207 (D) |
| (42) | structure with F | 6-(4-fluorophenyl)-5H-indeno[1,2-c]isoquinoline-5,11(6H)-dione | 215 | 12 | 63 | Orange Solid | 277-278 |
| (43) | structure with Cl | 6-(4-chlorophenyl)-5H-indeno[1,2-c]isoquinoline-5,11(6H)-dione | 240 | 12 | 67 | Orange Solid | 314-315 |
| (44) | structure | 6-pentyl-indeno[1,2-c]isoquinoline-5,11(6H)-dione | 200 | 24 | 63 | Red Solid | 144-145 |
| (45) | structure with Ph | 6-(4-phenylbutyl)-5H-indeno[1,2-c]isoquinoline-5,11(6H)-dione | 243 | 24 | 64 | Orange Solid | 139-140 |
| (46) | structure | 6-(3-methoxypropyl)-5H-indeno[1,2-c]isoquinoline-5,11(6H)-dione | 166 | 12 | 52 | Red Solid | 158-160 |

NMR spectra and mass data of Compounds (1) to (46), (4a) and (5a) are listed as follows.

Compound (1): $^1$H-NMR (400 MHz, CDCl$_3$) δ 8.69 (d, J=8.0 Hz, 1H), 8.36 (d, J=8.2 Hz, 1H), 7.75-7.71 (m, 1H), 7.68-7.63 (m, 2H), 7.49-7.41 (m, 3H), 4.08 (s, 3H); $^{13}$C-NMR (100 MHz, CDCl$_3$) δ 190.7, 163.7, 156.3, 137.9, 135.4, 134.1, 133.3, 132.4, 131.3, 128.8, 127.4, 123.7, 123.6, 123.5, 123.0, 108.6, 32.5; HRMS (ESI) m/z calcd for C$_{17}$H$_{12}$NO$_2$ (M$^+$+H) 262.0868, found 262.0869.

Compound (2): $^1$H-NMR (400 MHz, (CD$_3$)$_2$SO) δ 8.39 (d, J=8.0 Hz, 1H), 8.17 (d, J=8.0 Hz, 1H), 7.87-7.73 (m, 2H), 7.54-7.41 (m, 4H); $^{13}$C-NMR (100 MHz, (CD$_3$)$_2$SO) δ 190.2, 164.6, 157.7, 137.6, 135.1, 134.1, 133.6, 131.8, 128.3, 126.7, 124.5, 122.9, 122.5, 121.2, 105.9; HRMS (ESI) m/z calcd for. C$_{16}$H$_{10}$NO$_2$ (M$^+$+H) 248.0706, found 248.0705.

Compound (3): $^1$H-NMR (400 MHz, CDCl$_3$) δ 8.70 (d, J=8.1 Hz, 1H), 8.34 (d, J=8.1 Hz, 1H), 7.74-7.70 (m, 1H), 7.63 (d, J=6.7 Hz, 1H), 7.55 (d, J=7.4 Hz, 1H), 7.48-7.38 (m, 3H), 4.60 (q, J=7.1 Hz, 2H), 1.55 (t, J=7.1 Hz, 3H); $^{13}$C-NMR (100 MHz, CDCl$_3$) δ 190.7, 163.5, 155.7, 137.3, 135.5, 134.0, 133.4, 132.5, 131.2, 128.6, 127.4, 123.8, 123.7, 123.5, 122.7, 108.8, 40.2, 14.7; HRMS (ESI) m/z calcd for C$_{18}$H$_{14}$NO$_2$ (M$^+$+H) 276.1025, found 276.1026.

Compound (4): $^1$H-NMR (600 MHz, CDCl$_3$) δ 8.68 (d, J=8.0 Hz, 1H), 8.33 (d, J=8.0 Hz, 1H), 7.73-7.70 (m, 1H), 7.58 (d, J=6.2 Hz, 1H), 7.47-7.44 (m, 2H), 7.40-7.33 (m, 2H), 6.14-6.08 (m, 1H), 5.30 (d, J=10.4 Hz, 1H), 5.20-5.16 (m, 3H); $^{13}$C-NMR (150 MHz, CDCl$_3$) δ 190.7, 163.3, 156.0, 137.1, 135.3, 134.1, 133.3, 132.5, 131.6, 131.1, 128.8, 127.4, 123.7, 123.7, 123.3, 123.1, 117.6, 108.8, 46.6; HRMS (ESI) m/z calcd for C$_{19}$H$_{14}$NO$_2$ (M$^+$+H) 288.1025, found 288.1024.

Compound (5): $^1$H-NMR (400 MHz, CDCl$_3$) δ 8.76 (d, J=8.1 Hz, 1H), 8.38 (d, J=8.2 Hz, 1H), 7.79-7.75 (m, 1H), 7.62-7.60 (d, J=6.8 Hz, 1H), 7.51-7.48 (m, 1H), 7.37-7.23 (m, 8H), 5.80 (s, 2H); $^{13}$C-NMR (125 MHz, CDCl$_3$+CF$_3$CO$_2$D) δ 191.5, 164.7, 156.3, 137.0, 135.0, 134.9, 133.9, 132.8, 131.5, 129.4, 128.9, 128.1, 128.1, 125.9, 123.9, 123.4, 109.9, 48.9; HRMS (ESI) m/z calcd for C$_{23}$H$_{16}$NO$_2$ (M$^+$+H) 338.1181, found 338.1183.

Compound (6): $^1$H-NMR (400 MHz, CDCl$_3$) δ 8.74 (d, J=7.9 Hz, 1H), 8.37 (d, J=8.1 Hz, 1H), 7.80 (m, 1H), 7.65-7.64 (m, 3H), 7.56-7.44 (m, 4H), 7.26-7.21 (m, 1H), 7.01-6.98 (m, 1H), 5.49 (d, J=7.5 Hz, 1H); $^{13}$C-NMR (150 MHz, CDCl$_3$) δ 190.8, 163.8, 155.5, 137.7, 137.3, 135.0, 134.4, 132.9, 132.9, 130.9, 130.3, 128.9, 128.9, 127.5, 124.2, 123.9, 123.0, 122.6, 108.4; HRMS (ESI) m/z calcd for C$_{22}$H$_{14}$NO$_2$ (M$^+$+H) 324.1025, found 324.1027.

Compound (7): $^1$H-NMR (400 MHz, CDCl$_3$) δ 8.71 (d, J=8.2 Hz, 1H), 8.33 (d, J=8.0 Hz, 1H), 7.75-7.68 (m, 2H), 7.64 (d, J=7.9 Hz, 1H), 7.49-7.44 (m, 2H), 7.42-7.39 (m, 1H), 4.69 (t, J=7.6 Hz, 2H), 3.74 (t, J=4.6 Hz, 4H), 2.82 (t, J=7.6 Hz, 2H), 2.62 (t, J=4.6 Hz, 4H); $^{13}$C-NMR (150 MHz, CDCl$_3$) δ 190.6, 163.5, 155.8, 137.4, 135.4, 134.1, 133.5, 132.5, 131.2, 128.6, 127.5, 123.7, 123.6, 123.5, 122.6, 108.9, 67.2, 56.9, 54.2, 42.6; HRMS (ESI) m/z calcd for C$_{22}$H$_{21}$N$_2$O$_3$ (M$^+$+H) 361.1552, found 361.1553.

Compound (8): $^1$H-NMR (600 MHz, CDCl$_3$) δ 8.70 (d, J=8.0 Hz, 1H), 8.33 (d, J=8.3 Hz, 1H), 7.73-7.70 (m, 2H), 7.61 (d, J=7.0 Hz, 1H), 7.47-7.42 (m, 2H), 7.38-7.36 (m, 1H), 4.71 (t, J=6.4 Hz, 2H), 3.85 (t, J=6.4 Hz, 2H), 3.38 (s, 3H); $^{13}$C-NMR (150 MHz, CDCl$_3$) δ 190.8, 163.8, 156.4, 137.7, 135.3, 134.1, 133.3, 132.6, 131.1, 128.6, 127.4, 123.8, 123.6, 123.3, 108.7, 70.1, 59.5, 44.8; HRMS (ESI) m/z calcd for C$_{19}$H$_{16}$NO$_3$ (M$^+$+H) 306.1130, found 306.1130.

Compound (9): $^1$H-NMR (400 MHz, CDCl$_3$+CF$_3$CO$_2$D) δ 9.21 (s, 1H), 8.86 (d, J=8.9 Hz, 1H), 8.58 (d, J=8.9 Hz, 1H), 7.80 (d, J=7.1 Hz, 1H), 7.76 (d, J=7.1 Hz, 1H), 7.62-7.54 (m, 2H), 4.19 (s, 3H); $^{13}$C-NMR (150 MHz, CDCl$_3$+CF$_3$CO$_2$D) δ 191.2, 163.9, 146.3, 137.0, 136.8, 135.0, 134.5, 133.0, 128.6, 125.3, 125.2, 124.8, 124.5, 123.0, 108.5, 33.5; HRMS (ESI) m/z calcd for C$_{17}$H$_{11}$N$_2$O$_4$ (M$^+$+H) 307.0719, found 307.0716.

Compound (10): $^1$H-NMR (400 MHz, CDCl$_3$) δ 8.56 (d, J=8.7 Hz, 1H), 8.50 (s, 1H), 7.80 (d, J=8.6 Hz, 1H), 7.68-7.64 (m, 2H), 7.46-7.40 (m, 2H), 4.07 (s, 3H); $^{13}$C-NMR (150 MHz, CDCl$_3$+CF$_3$CO$_2$D) δ 191.7, 163.7, 156.4, 138.1, 137.3, 134.7, 134.3, 132.1, 131.3, 131.1, 125.4, 124.5, 124.4, 123.7, 122.0, 109.4, 33.4; HRMS (ESI) m/z calcd for C$_{17}$H$_{11}$BrNO$_2$ (M$^+$+H) 339.9973, found 339.9970.

Compound (11): $^1$H-NMR (400 MHz, CDCl$_3$) δ 8.70 (d, J=8.5 Hz, 1H), 8.34 (s, 1H), 7.69 (d, J=8.3 Hz, 1H), 7.61 (d, J=8.3 Hz, 1H), 7.37-7.21 (m, 8H), 5.79 (s, 2H); $^{13}$C-NMR (100 MHz, CDCl$_3$) δ 190.5, 162.7, 156.3, 137.1, 135.3, 135.1, 134.8, 133.6, 131.3, 131.0, 129.4, 128.4, 128.0, 125.9, 125.5, 124.9, 123.6, 123.2, 108.6, 48.5; HRMS (ESI) m/z calcd for C$_{23}$H$_{15}$ClNO$_2$ (M+$^+$H) 372.0791, found 372.0789.

Compound (12): $^1$H-NMR (400 MHz, CDCl$_3$) δ 8.59 (d, J=8.4 Hz, 1H), 7.74 (s, 1H), 7.64-7.55 (m, 2H), 7.41-7.33 (m, 3H), 4.06 (s, 3H), 3.93 (s, 3H); $^{13}$C-NMR (150 MHz, CDCl$_3$) δ 190.8, 163.4, 159.2, 154.0, 138.3, 135.3, 133.3, 130.8, 126.5, 125.4, 125.1, 124.4, 123.5, 122.5, 109.0, 108.8, 55.8, 32.6; HRMS (ESI) m/z calcd for C$_{18}$H$_{14}$NO$_3$ (M$^+$+H) 292.0974, found 292.0973.

Compound (13): $^1$H-NMR (400 MHz, CDCl$_3$) δ 8.10 (s, 1H), 7.70 (s, 1H), 7.62-7.58 (m, 2H), 7.43-7.34 (m, 2H), 4.07 (s, 3H), 4.05 (s, 3H), 4.00 (s, 3H); $^{13}$C-NMR (100 MHz, CDCl$_3$) δ 190.9, 162.8, 155.1, 154.8, 149.7, 138.2, 135.4, 133.3, 130.9, 128.1, 123.4, 122.7, 117.9, 108.5, 103.7, 56.5, 56.3, 32.5; HRMS (ESI) m/z calcd for C$_{19}$H$_{16}$NO$_4$ (M$^+$+H) 322.1079, found 22.1079.

Compound (14): $^1$H-NMR (400 MHz, CDCl$_3$) δ 8.18 (s, 1H), 7.73 (s, 1H), 7.56 (d, J=6.6 Hz, 1H), 7.37-7.33 (m, 2H), 7.28-7.22 (m, 6H), 5.79 (s, 2H), 4.09 (s, 3H), 3.99 (s, 3H); $^{13}$C-NMR (100 MHz, CDCl$_3$) δ 191.1, 162.9, 155.3, 154.9, 149.8, 137.6, 135.8, 135.3, 133.4, 130.7, 129.3, 128.4, 127.8, 126.0, 123.2, 122.7, 118.0, 108.9, 108.7, 103.8, 56.6, 56.3, 48.3; HRMS (EST) m/z calcd for C$_{25}$H$_{20}$NO$_4$ (M$^+$+H) 398.1392, found 398.1390.

Compound (15): $^1$H-NMR (400 MHz, CDCl$_3$) δ 8.11 (s, 1H), 7.69 (s, 1H), 7.63-7.60 (m, 2H), 7.44-7.35 (m, 2H), 6.10 (s, 2H), 4.04 (s, 3H); $^{13}$C-NMR (150 MHz, CDCl$_3$) δ 190.8, 165.4, 159.2, 154.0, 138.3, 135.3, 133.3, 130.8, 126.5, 125.4, 125.1, 124.4, 123.5, 122.5, 109.0, 108.8, 55.8, 32.6; HRMS (ESI) m/z calcd for C$_{18}$H$_{12}$NO$_4$ (M$^+$+H) 306.0766, found 306.0765.

Compound (16): $^1$H-NMR (400 MHz, CDCl$_3$) δ 8.17 (s, 1H), 7.70 (s, 1H), 7.57 (d, J=6.4 Hz, 1H), 7.35-7.33 (m, 2H), 7.26-7.21 (m, 6H), 6.11 (s, 2H), 5.76 (s, 2H); 13C-NMR (100 MHz, CDCl$_3$) δ 190.8, 162.8, 154.9, 153.7, 148.3, 137.3, 135.7, 135.2, 133.5, 130.8, 130.2, 129.3, 128.3, 127.9, 125.9, 123.4, 122.8, 119.6, 109.1, 106.8, 102.2, 102.0, 48.3; HRMS (ESI) m/z calcd for C$_{24}$H$_{16}$NO$_4$ (M$^+$+H) 382.1079, found 382.1079.

Compound (17): $^1$H-NMR (400 MHz, CDCl$_3$) δ 8.59 (d, J=8.0 Hz, 1H), 8.31 (d, J=8.4 Hz, 1H), 7.70-7.66 (m, 1H), 7.42-7.39 (m, 1H), 7.22 (s, 1H), 7.18 (s, 1H), 4.03 (s, 3H), 4.00 (s, 3H), 3.97 (s, 3H); $^{13}$C-NMR (125 MHz, CDCl$_3$+CF$_3$CO$_2$D) δ 192.7, 156.1, 152.6, 151.2, 135.2, 132.8, 131.4, 128.6, 128.4, 127.8, 123.3, 122.5, 108.9, 108.8, 57.0, 56.7, 33.2; HRMS (ESI) m/z calcd for $C_{19}H_{16}NO_4$ (M$^+$+H) 322.1079, found 322.1078.

Compound (18): $^1$H-NMR (400 MHz, CDCl$_3$) δ 8.68 (d, J=8.1 Hz, 1H), 8.38 (d, J=8.1 Hz, 1H), 7.77-7.73 (m, 1H), 7.49-7.45 (m, 1H), 7.40-7.36 (m, 2H), 7.31 (d, J=7.1 Hz, 1H), 7.25 (d, J=7.5 Hz, 2H), 7.17 (s, 1H), 6.78 (s, 1H), 5.81 (s, 1H), 3.93 (s, 3H), 3.61 (s, 3H); $^{13}$C-NMR (150 MHz, CDCl$_3$) δ 190.6, 163.8, 156.3, 151.9, 150.6, 135.9, 134.1, 132.9, 130.3, 129.4, 128.9, 128.5, 127.9, 126.8, 125.5, 123.2, 123.0, 108.4, 108.0, 107.4, 56.5, 56.4, 48.2; HRMS (ESI) m/z calcd for $C_{25}H_{20}NO_4$ (M$^+$+H) 398.1392, found 398.1391.

Compound (19): $^1$H-NMR (500 MHz, CDCl$_3$+CF$_3$CO$_2$D) δ 9.11 (s, 1H), 8.69 (d, J=9.0 Hz, 1H), 8.46 (d, J=9.0 Hz, 1H), 7.33 (s, 1H), 7.24 (s, 1H), 4.09 (s, 3H), 4.03 (s, 3H), 4.00 (s, 3H); $^{13}$C-NMR (125 MHz, CDCl$_3$+CF$_3$CO$_2$D) δ; 190.7, 163.7, 159.5, 152.8, 152.3, 145.7, 137.0, 130.1, 129.0, 128.5, 125.4, 124.6, 122.0, 109.2, 108.6, 107.6, 57.0, 56.8, 33.2; HRMS (ESI) m/z calcd for $C_{19}H_{15}N_2O_6$ (M$^+$+H) 367.0930, found 367.0926.

Compound (20): $^1$H-NMR (400 MHz, CDCl$_3$) δ 8.47-8.44 (m, 2H), 7.75 (d, J=8.3 Hz, 1H), 7.22 (s, 1H), 7.17 (s, 1H), 4.02 (s, 3H), 4.00 (s, 3H), 3.97 (s, 3H); $^{13}$C-NMR (125 MHz, CDCl$_3$+CF$_3$CO$_2$D) δ 190.7, 163.0, 156.2, 152.4, 151.3, 137.5, 131.1, 128.4, 124.8, 123.7, 120.8, 108.5, 108.1, 107.8, 56.9, 56.6, 32.8; HRMS (ESI) m/z calcd for $C_{19}H_{14}BrNO_4$ (M$^+$+H) 399.0106, found 399.0109.

Compound (21): $^1$H-NMR (500 MHz, CDCl$_3$) δ 8.03 (s, 1H), 7.66 (s, 1H), 7.21 (s, 1H), 7.15 (s, 1H), 6.08 (s, 2H), 4.01 (s, 3H), 3.99 (s, 3H), 3.96 (s, 3H); $^{13}$C-NMR (150 MHz, CDCl$_3$+CF$_3$CO$_2$D) δ 193.1, 155.2, 153.8, 152.8, 150.8, 149.2, 131.8, 131.4, 128.2, 125.2, 109.4, 108.9, 105.6, 102.8, 101.2, 56.9, 56.7, 33.5; HRMS (ESI) m/z calcd for $C_{20}H_{16}NO_6$ (M$^+$+H) 366.0978, found 366.0976.

Compound (22): $^1$H-NMR (500 MHz, CDCl$_3$+CF$_3$CO$_2$D) δ 8.03 (s, 1H), 7.63 (s, 1H), 7.39-7.36 (m, 2H), 7.33-7.30 (m, 1H), 7.24 (s, 1H), 7.17 (d, J=7.4 Hz, 2H), 6.73 (s, 1H), 6.15 (s, 2H), 5.82 (s, 2H), 3.91 (s, 3H), 3.59 (s, 3H); $^{13}$C-NMR (125 MHz, CDCl$_3$+CF$_3$CO$_2$D) δ 192.9, 164.4, 155.1, 154.7, 152.7, 150.5, 149.0, 134.6, 131.5, 130.8, 129.7, 128.5, 127.9, 125.3, 118.3, 110.3, 108.9, 106.2, 102.7, 101.3, 56.6, 56.5, 49.3; HRMS (ESI) m/z calcd for $C_{26}H_{20}NO_6$ (M$^+$+H) 442.1291, found 442.1292.

Compound (23): $^1$H-NMR (400 MHz, CDCl$_3$) δ 8.59 (d, J=7.8 Hz, 1H), 8.32 (d, J=8.2 Hz, 1H), 7.71-7.67 (m, 1H), 7.43-7.39 (m, 1H), 7.19 (s, 1H), 7.13 (s, 1H), 6.10 (s, 2H), 4.00 (s, 3H); $^{13}$C-NMR (150 MHz, CDCl$_3$+CF$_3$CO$_2$D) δ 191.1, 155.5, 152.3, 149.9, 135.1, 132.9, 132.6, 129.9, 128.6, 127.8, 123.3, 122.3, 109.5, 106.5, 106.2, 103.3, 33.1; HRMS (ESI) m/z calcd for $C_{18}H_{12}NO_4$ (M$^+$+H) 306.0766, found 306.0763.

Compound (24): $^1$H-NMR (400 MHz, CDCl$_3$) δ 8.66 (d, J=8.5 Hz, 1H), 8.34 (d, J=8.0 Hz, 1H), 7.75-7.71 (m, 1H), 7.46-7.42 (m, 1H), 7.38-7.34 (m, 2H), 7.30-7.20 (m, 3H), 7.09 (s, 1H), 6.80 (s, 1H), 6.00 (s, 2H), 5.73 (s, 2H); $^{13}$C-NMR (125 MHz, CDCl$_3$+CF$_3$CO$_2$D) δ 191.0, 155.3, 152.3, 149.8, 135.2, 132.8, 132.3, 130.7, 130.0, 128.7, 127.8, 123.4, 122.5, 118.1, 109.6, 106.3, 106.2, 103.1, 47.2; HRMS (ESI) m/z calcd for $C_{24}H_{16}NO_4$ (M$^+$+H) 382.1079, found 382.1079.

Compound (25): $^1$H-NMR (400 MHz, CDCl$_3$) δ 8.62 (d, J=8.5 Hz, 1H), 8.32 (d, J=8.0 Hz, 1H), 7.72-7.69 (m, 1H), 7.44-7.41 (m, 1H), 7.11 (s, 1H), 7.00 (s, 1H), 6.18-6.03 (m, 3H), 5.33 (d, J=10.4 Hz, 1H), 5.20-5.11 (m, 3H); $^{13}$C-NMR (100 MHz, CDCl$_3$) δ 189.5, 163.3, 151.5, 149.3, 134.1, 132.7, 132.3, 131.5, 130.7, 128.8, 126.7, 123.3, 123.0, 117.6, 105.8, 105.6, 103.9, 102.8, 46.3; HRMS (ESI) m/z calcd for $C_{20}H_{14}NO_4$ (M$^+$+H) 322.0923, found 332.0923.

Compound (26): $^1$H-NMR (400 MHz, CDCl$_3$) δ 8.66 (d, J=8.4 Hz, 1H), 8.32 (d, J=7.7 Hz, 1H), 7.73-7.70 (m, 1H), 7.46-7.42 (m, 1H), 7.35 (s, 1H), 7.14 (s, 1H), 6.13 (s, 2H), 4.66 (t, J=5.9 Hz, 2H), 3.87 (t, J=6.2 Hz, 2H), 3.40 (s, 3H); $^{13}$C-NMR (125 MHz, CDCl$_3$+CF$_3$CO$_2$D) δ 190.9, 155.4, 152.3, 49.7, 135.2, 132.8, 132.8, 130.1, 128.4, 127.7, 123.4, 109.8, 106.4, 106.1, 103.2, 70.0, 60.0, 45.0; HRMS (ESI) m/z calcd for $C_{20}H_{16}NO_5$ (M$^+$+H) 350.1028, found 350.1026.

Compound (27): $^1$H-NMR (400 MHz, CDCl$_3$) δ 8.48-8.45 (m, 2H), 7.76 (d, J=9.8 Hz, 1H); 7.19 (s, 1H), 7.13 (s, 1H), 6.11 (s, 2H), 4.00 (s, 3H); $^{13}$C-NMR (125 MHz, CDCl$_3$+CF$_3$CO$_2$D) δ 190.6, 163.9, 155.7, 152.4, 150.0, 138.1, 132.8, 131.2, 131.1, 130.0, 124.9, 123.7, 121.4, 108.8, 106.6, 106.2, 103.3, 33.2; HRMS (ESI) m/z calcd for $C_{18}H_{11}BrNO_4$ (M$^+$+H) 383.9871, found 383.9866.

Compound (28): $^1$H-NMR (400 MHz, CDCl$_3$) δ 8.51 (d, J=8.8 Hz, 1H); 7.7 (s, 1H), 7.31-7.26 (m, 2H), 7.13 (s, 1H), 7.09 (s, 1H), 6.08 (s, 2H), 3.99 (s, 3H), 3.91 (s, 1H); $^{13}$C-NMR (100 MHz, CDCl$_3$+CF$_3$CO$_2$D) δ 192.2, 159.3, 153.2, 152.7, 149.6, 133.6, 129.4, 127.3, 126.4, 125.1, 108.2, 106.9, 106.1, 103.3, 55.9, 33.4; HRMS (ESI) m/z calcd for $C_{19}H_{14}NO_5$ (M$^+$+H) 336.0872, found 336.0868.

Compound (29): $^1$H-NMR (400 MHz, CDCl$_3$) δ 8.00 (s, 1H), 7.66 (s, 1H), 7.14 (s, 1H), 7.08 (s, 1H), 6.09 (s, 2H), 4.05 (s, 3H), 3.99 (s, 311), 3.99 (s, 3H); $^{13}$C-NMR (150 MHz, CDCl$_3$+CF$_3$CO$_2$D) δ 191.2, 156.0, 153.8, 152.4, 149.8, 149.6, 133.3, 129.8, 129.2, 116.8, 109.6, 108.0, 106.5, 105.9, 103.2, 103.0, 56.6, 56.3, 33.2; HRMS (ESI) m/z calcd for $C_{20}H_{16}NO_6$ (M$^+$+H) 366.0978, found 366.0978.

Compound (30): $^1$H-NMR (400 MHz, CDCl$_3$) δ 8.05 (s, 1H), 7.65 (s, 1H), 7.43 (s, 1H), 7.09 (s, 1H), 6.10 (s, 1H), 4.55-4.48 (m, 2H), 4.05 (s, 3H), 3.99 (s, 3H), 3.79-3.92 (m, 4H), 2.60-2.48 (in, 6H), 2.06-1.97 (m, 2H); $^{13}$C-NMR (100 MHz, CDCl$_3$+CF$_3$CO$_2$D) δ 191.2, 152.9, 152.5, 150.1, 150.0, 131.9, 129.6, 129.4, 116.3, 110.4, 107.5, 106.7, 104.8, 103.5, 103.2, 64.2, 56.7, 56.2, 55.5, 52.9, 42.0, 24.3; HRMS (ESI) m/z calcd for $C_{26}H_{27}N_2O_7$ (M$^+$+H) 479.1818, found 479.1820.

Compound (31): $^1$H-NMR (400 MHz, CDCl$_3$) δ 8.05 (s, 1H), 7.66 (s, 1H), 7.64-7.59 (m, 1H), 7.19-7.13 (m, 1H), 7.08 (s, 1H), 7.07-7.03 (m, 1H), 6.43 (s, 1H), 6.09 (s, 2H), 4.47 (t, J=6.8 Hz, 2H), 4.22 (t, J=6.8 Hz, 2H), 4.05 (s, 3H), 4.00 (s, 3H), 2.39-2.32 (m, 2H); $^{13}$C-NMR (100 MHz, CDCl$_3$+CF$_3$CO$_2$D) δ 191.8, 156.5, 153.1, 152.8, 150.1, 135.3, 132.2, 129.8, 129.6, 121.9, 121.0, 116.4, 110.5, 107.7, 107.1, 104.9, 103.6, 103.3, 56.7, 56.3, 47.5, 42.1, 30.3; HRMS (ESI) m/z calcd for $C_{25}H_{22}N_3O_6$ (M$^+$+H) 460.1509, found 460.1507.

Compound (32): $^1$H-NMR (400 MHz, CDCl$_3$) δ 9.16 (s, 1H), 7.82 (d, J=8.0 Hz, 1H), 7.75 (d, J=7.3 Hz, 1H), 7.69-7.64 (m, 4H), 7.53-7.47 (m, 3H), 7.32-7.28 (m, 1H), 7.06-7.02 (m, 1H), 5.56 (d, J=7.6 Hz, 1H), 3.01 (s, 3H); $^{13}$C-NMR (125 MHz, CDCl$_3$+CF$_3$CO$_2$D) δ 189.8, 166.0, 160.7, 151.3, 143.0, 141.0, 138.1, 135.8, 135.6, 135.2, 135.1, 134.8, 132.1, 131.3, 130.5, 129.9, 128.0, 127.7, 127.0, 126.2, 125.3, 118.2, 99.7, 16.0; HRMS (ESI) m/z calcd for $C_{26}H_{17}N_2O_2$ (M$^+$+H) 389.1290, found 389.1288.

Compound (33): $^1$H-NMR (400 MHz, CDCl$_3$) δ 7.94 (d, J=5.2 Hz, 1H), 7.86 (d, J=5.2 Hz, 1H), 7.37-7.22 (m, 7H), 5.81 (s, 2H); $^{13}$C-NMR (100 MHz, CDCl$_3$) δ 189.1, 159.5, 156.6, 140.3, 137.7, 136.8, 135.4, 134.9, 133.6, 131.1, 129.4, 128.8, 128.0, 126.0, 123.8, 123.2, 123.0, 110.2, 47.9; HRMS (ESI) m/z calcd for $C_{21}H_{14}NO_2S$ (M$^+$+H) 344.0745, found 344.0745.

Compound (34): $^1$H-NMR (500 MHz, CDCl$_3$+CF$_3$CO$_2$D) δ 8.74 (d, J=8.1 Hz, 1H), 8.37 (d, J=8.1 Hz, 1H), 7.97 (d, J=7.9 Hz, 1H), 7.83-7.80 (m, 1H), 7.59-7.53 (m, 2H), 7.32-7.21 (m, 3H), 7.03-7.00 (m, 1H), 6.96 (d, J=7.4 Hz, 1H), 6.74 (d, J=7.8 Hz, 1H), 5.65 (s, 2H); $^{13}$C-NMR (125 MHz, CDCl$_3$+CF$_3$CO$_2$D) δ 191.5, 164.4, 156.0, 140.2, 136.6, 135.1, 134.7, 134.1, 132.8, 131.5, 129.8, 129.3, 129.0, 128.2, 125.9, 124.0, 123.3, 123.0, 116.0, 113.7, 110.0, 96.7, 54.4; HRMS (ESI) m/z calcd for $C_{23}H_{15}INO_2$ (M$^+$+H) 464.0147, found 464.0151.

Compound (35): $^1$H-NMR (400 MHz, CDCl$_3$) δ 8.75 (d, J=8.1 Hz, 1H), 8.40 (d, J=7.8 Hz, 1H), 8.32 (d, J=8.2 Hz, 1H), 7.94-7.86 (m, 3H), 7.82-7.79 (m, 1H), 7.61-7.58 (m, 2H), 7.53-7.49 (m, 1H), 7.04-7.00 (m, 1H), 5.57 (d, J=7.1 Hz, 1H); $^{13}$C-NMR (125 MHz, CDCl$_3$+CF$_3$CO$_2$D) δ 191.5, 154.6, 146.4, 137.7, 136.7, 135.6, 135.4, 134.4, 133.6, 133.1, 132.1, 131.8, 131.6, 131.2, 129.1, 128.3, 126.8, 124.5, 124.1, 124.0, 123.5, 121.2, 110.2; HRMS (ESI) m/z calcd for $C_{22}H_{13}N_2O_4$ (M$^+$+H) 369.0875, found 369.0876.

Compound (36): $^1$H-NMR (400 MHz, CDCl$_3$) δ 8.67 (d, J=8.1 Hz, 1H), 8.36 (d, J=7.6 Hz, 1H), 7.78-7.65 (m, 4H), 7.53-7.45 (m, 3H), 7.16 (s, 1H), 5.11 (s, 1H), 3.92 (s, 3H), 3.39 (s, 3H); $^{13}$C-NMR (100 MHz, CDCl$_3$+CF$_3$CO$_2$D) δ 192.6, 155.1, 152.0, 150.6, 136.8, 135.6, 133.4, 131.0, 130.9, 130.7, 129.0, 128.9, 127.9, 127.7, 123.5, 108.4, 107.8, 56.6, 55.9; HRMS (ESI) m/z calcd for $C_{24}H_{18}NO_4$ (M$^+$+H) 384.1236, found 384.1239.

Compound (37): $^1$H-NMR (600 MHz, CDCl$_3$) δ 8.65 (d, J=7.9 Hz, 1H), 8.35 (d, J=7.3 Hz, 1H), 7.77 (d, J=1.4 Hz, 1H), 7.74-7.72 (m, 1H), 7.55 (dd, J=7.7, 1.5 Hz, 1H), 7.50-7.47 (m, 2H), 4.05 (s, 3H). $^{13}$C-NMR (150 MHz, CDCl$_3$) δ 189.4, 163.5, 155.0, 139.8, 134.2, 133.9, 133.9, 132.1, 128.9, 127.8, 126.4, 124.5, 123.9, 123.8, 109.3, 32.5; HRMS (EST) m/z calcd for $C_{17}H_{11}NO_2Br$ (M$^+$+H) 339.9973, found 339.9976.

Compound (38): $^1$H-NMR (600 MHz, CDCl$_3$) δ 8.63 (d, J=8.0 Hz, 1H), 8.34 (d, J=8.1 Hz, 1H), 7.73-7.70 (m, 2H), 7.57 (dd, J=8.0, 1.9 Hz, 1H), 7.51-7.46 (m, 2H), 4.03 (s, 3H); $^{13}$C-NMR (150 MHz, CDCl$_3$) δ 189.0, 163.5, 156.0, 137.1, 136.5, 135.6, 134.2, 132.1, 128.9, 127.7, 127.0, 125.8, 124.1, 123.7, 123.7, 108.6, 32.5; HRMS (ESI) m/z calcd for $C_{17}H_{11}NO_2Br$ (M$^+$+H) 339.9973, found 339.9976.

Compound (39): $^1$H-NMR (400 MHz, CDCl$_3$+CF$_3$CO$_2$D) δ 8.66 (d, J=8.0 Hz, 1H), 8.33 (d, J=8.0 Hz, 1H), 7.92 (d, J=7.5 Hz, 1H), 7.82 (t, J=7.6 Hz, 1H), 7.68-7.64 (m, 1H), 7.61-7.57 (m, 2H), 4.16 (3H); $^{13}$C-NMR (100 MHz, CDCl$_3$+CF$_3$CO$_2$D) δ 185.0, 165.0, 153.7, 146.3, 139.6, 135.5, 135.3, 131.8, 129.2, 128.8, 125.7, 125.6, 125.1, 124.0, 123.5, 110.6, 33.5; HRMS (ESI) m/z calcd for $C_{17}H_{11}N_2O_4$ (M$^+$+H) 307.0719, found 307.0721.

Compound (40): $^1$H-NMR (400 MHz, CDCl$_3$) δ 8.59 (d, J=8.7 Hz, 1H), 7.92-7.90 (m, 1H), 7.72-7.68 (m, 1H), 7.63-7.61 (m, 1H), 7.52-7.40 (m, 4H), 3.89 (s, 3H); $^{13}$C-NMR (100 MHz, CDCl$_3$) δ 190.5, 157.7, 137.8, 134.0, 133.5, 133.4, 131.6, 129.2, 128.1, 127.7, 125.3, 123.5, 122.4, 122.3, 110.0, 33.1.

Compound (4a): $^1$H-NMR (400 MHz, CDCl$_3$+(CD$_3$)$_2$SO) δ 8.46 (d, J=8.1 Hz, 1H), 8.13 (d, J=7.9 Hz, 1H), 7.57-7.53 (m, 1H), 7.30-7.27 (m, 2H), 7.08-7.00 (m, 4H), 6.88-6.85 (m, 2H), 5.55 (d, J=7.4 Hz, 1H); $^{13}$C-NMR (100 MHz, CDCl$_3$1+(CD$_3$)$_2$SO) δ 190.4, 162.6, 155.9, 141.0, 136.6, 134.1, 133.8, 132.9, 132.5, 130.9, 130.5, 129.0, 128.3, 126.8, 124.2, 123.8, 123.1, 122.2, 121.9, 120.7, 118.7, 108.2; HRMS (ESI) m/z calcd for $C_{23}H_{14}NO_2$ (M$^+$) 336.1025, found 336.1026.

Compound (5a): $^1$H-NMR (400 MHz, CDCl$_3$) δ 8.56 (d, J=8.0 Hz, 1H), 8.41 (d, J=7.5 Hz, 1H), 7.86 (d, J=8.1 Hz, 1H), 7.76-7.71 (m, 3H), 7.64 (d, J=7.0 Hz, 1H), 7.56-7.52 (m, 2H), 7.50-7.46 (m, 2H), 5.46 (s, 2H); $^{13}$C-NMR (100 MHz, CDCl$_3$) δ 189.5, 163.0, 137.2, 136.3, 135.7, 135.5, 134.1, 134.0, 132.9, 132.6, 132.2, 131.7, 131.6, 129.9, 129.5, 129.2, 128.6, 127.1, 124.7, 123.8, 122.8, 107.5, 47.9; HRMS (ESI) m/z calcd for $C_{22}H_{13}N_2O$ (M$^+$) 321.1028, found 321.1028.

Compound (42): $^1$H-NMR (400 MHz, CDCl$_3$) δ 8.73 (d, J=8.1 Hz, 1H), 8.35 (d, J=8.0 Hz, 1H), 7.77 (t, J=7.6 Hz, 1H), 7.56 (d, J=7.0 Hz, 1H), 7.50 (t, J=7.7 Hz, 1H), 7.45-7.42 (m, 2H), 7.33 (t, J=8.4 Hz, 2H), 7.27-7.23 (m, 1H), 7.05 (t, J=7.6 Hz, 1H), 5.6 (d, J=7.5 Hz, 1H); $^{13}$C-NMR (100 MHz, CDCl$_3$) δ 190.5, 164.5, 163.6, 162.0, 155.2, 137.0, 134.7, 134.3, 133.4, 133.3, 132.7, 132.6, 130.8, 130.6, 130.5, 128.7, 127.4, 124.0, 123.7, 122.9, 122.2, 117.3, 117.1, 108.4; HRMS (ESI) m/z calcd for $C_{22}H_{13}NO_2F$ (M$^+$+H) 342.0930, found 342.0932.

Compound (43): $^1$H-NMR (400 MHz, CDCl$_3$) δ 8.71 (d, J=8.0 Hz, 1H), 8.33 (d, J=8.0 Hz, 1H), 7.76 (t, J=7.5 Hz, 1H), 7.62 (d, J=8.2 Hz, 2H), 7.55 (d, J=7.0 Hz, 1H), 7.48 (t, J=7.6 Hz, 1H), 7.40 (d, J=8.2 Hz, 2H), 7.27-7.23 (m, 1H), 7.07 (t, J=7.6 Hz, 1H), 5.65 (d, J=7.5 Hz, 1H); $^{13}$C-NMR (100 MHz, CDCl$_3$) δ 190.5, 163.5, 154.9, 136.9, 136.2, 135.9, 134.6, 134.3, 132.8, 132.7, 130.9, 130.3, 130.1, 128.7, 127.4, 123.9, 123.7, 123.0, 122.2, 108.4; HRMS (ESI) m/z calcd for $C_{22}H_{13}NO_2Cl$ (M$^+$+H) 358.0635, found 358.0625.

Compound (44): $^1$H-NMR (400 MHz, CDCl$_3$) δ 8.68 (d, J=8.0 Hz, 1H), 8.32 (d, J=8.2 Hz, 1H), 7.71 (td, J=8.1, 1.1 Hz, 1H), 7.61 (d, J=6.7 Hz, 1H), 7.45 (td, J=7.3, 1.2 Hz, 3H), 7.39 (qd, J=14.22, 1.5 Hz, 1H), 4.49 (t, J=8.0 Hz, 2H), 1.94-1.86 (m, 2H), 1.56-1.40 (m, 4H), 0.96 (t, J=7.1 Hz, 3H); $^{13}$C-NMR (100 MHz, CDCl$_3$) δ 190.4, 163.3, 155.6, 137.2, 135.3, 133.8, 133.2, 132.3, 131.0, 128.4, 127.1, 123.5, 123.2, 122.3, 108.5, 44.7, 29.1, 29.0, 22.4, 14.0; HRMS (ESI) m/z calcd for $C_{21}H_{20}NO_2$(M$^+$+H) 318.1494, found 318.1495.

Compound (45): $^1$H-NMR (400 MHz, CDCl$_3$) δ 8.66 (d, J=8.1 Hz, 1H), 8.31 (d, J=8.0 Hz, 1H), 7.69 (td, J=8.3, 1.3 Hz, 1H), 7.61-7.57 (m, 1H), 7.44 (td, J=8.2, 1.1 Hz, 1H), 7.37-7.26 (m, 6H), 7.21-7.17 (m, 2H), 4.49 (t, J=7.5 Hz, 2H), 2.73 (t, J=7.1 Hz, 2H), 1.97-1.82 (m, 4H); $^{13}$C-NMR (100 MHz, CDCl$_3$) δ 190.4, 163.4, 141.6, 137.1, 135.2, 133.8, 133.2, 132.3, 130.9, 128.5, 128.4, 127.2, 126.0, 123.5, 123.2, 122.2, 108.5, 44.5, 35.3, 28.9, 28.4; HRMS (ESI) m/z calcd for $C_{26}H_{22}NO_2$ (M$^+$+H) 380.1651, found 380.1656.

Compound (46): $^1$H-NMR (400 MHz, CDCl$_3$) δ 8.70 (d, J=8.2 Hz, 1H), 8.33 (d, J=8.0 Hz, 1H), 7.86 (d, J=7.5 Hz, 1H), 7.72 (td, J=8.2, 1.2 Hz, 1H), 7.61 (d, J=7.3 Hz, 1H), 7.48-7.42 (m, 2H), 7.38 (t, J=7.3 Hz, 1H), 4.66-4.62 (m, 2H), 3.61 (t, J=5.53 Hz, 2H), 3.42 (s, 3H), 2.21-2.14 (m, 2H); $^{13}$C-NMR (100 MHz, CDCl$_3$) δ 190.6, 163.5, 155.8, 137.0, 135.2, 133.8, 133.4, 132.4, 130.9, 128.3, 127.1, 123.5, 123.4, 123.3, 123.2, 108.5. 70.1, 59.0, 42.9, 29.5; HRMS (ESI) m/z calcd for $C_{20}H_{18}NO_3$ (M$^+$+H) 320.1287, found 320.1287.

The aforesaid data shows that the method of the present disclosure can be used to prepare clinical used indenoisoquinoline derivatives in a mild condition rapidly and effectively. For example, Compound (29) prepared in the present disclosure is a clinical used drug NSC314622, Compound

(30) is a clinical used drug LMP-400, and Compound (31) is a clinical used drug LMP-776. In the method of the present disclosure, only a little amount of Cu-containing catalyst is used to obtain the indenoisoquinoline derivatives. In addition, when water is used as a solvent in the method of the present disclosure, the use of organic solvents can be prevented to reduce the environmental pollution.

Although the present disclosure has been explained in relation to its embodiment, it is to be understood that many other possible modifications and variations can be made without departing from the spirit and scope of the disclosure as hereinafter claimed.

What is claimed is:

1. A method for preparing indenoisoquinoline derivatives represented by one of the following formulas (1) to (31), (34) to (39) and (41) to (46), comprising the following steps:

(1)
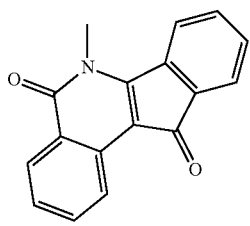

(2)
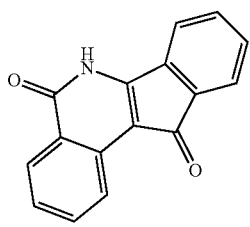

(3)

(4)
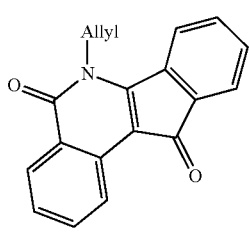

(5)
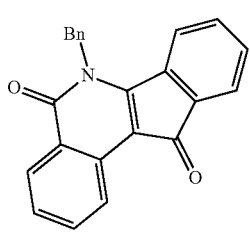

-continued (6)
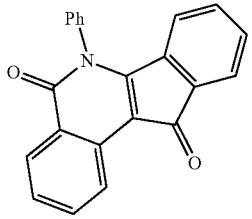

(7)
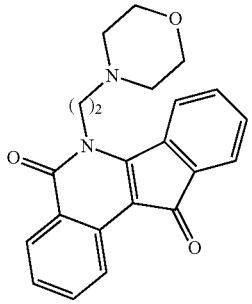

(8)
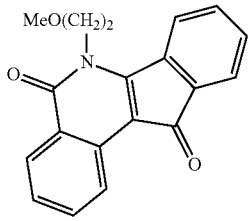

(9)

(10)
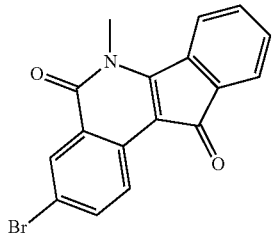

(11)
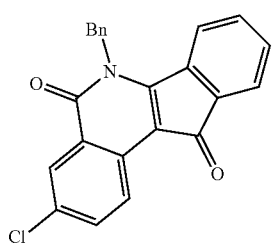

-continued
(12) 
(13) 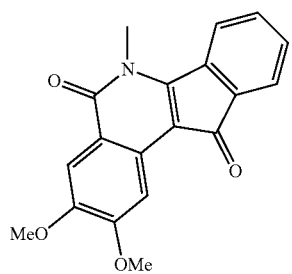
(14) 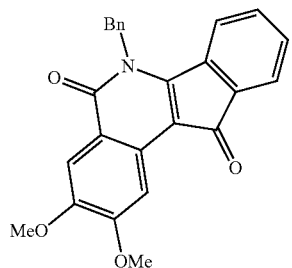
(15) 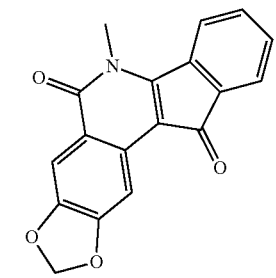
(16) 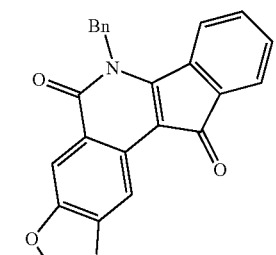
(17) 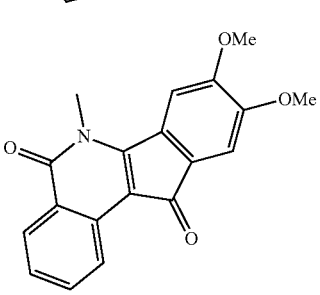
-continued
(18) 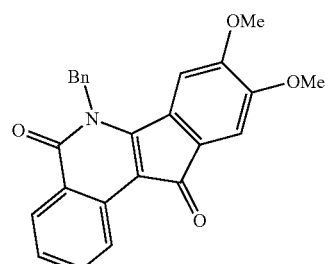
(19) 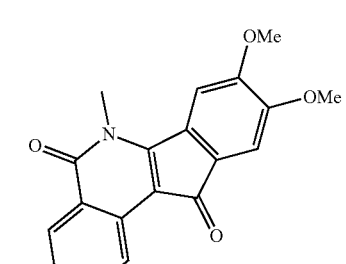
(20) 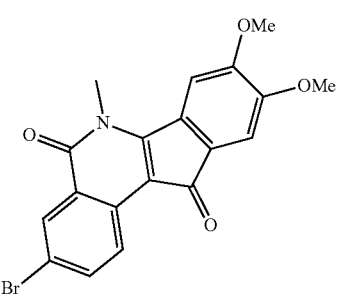
(21) 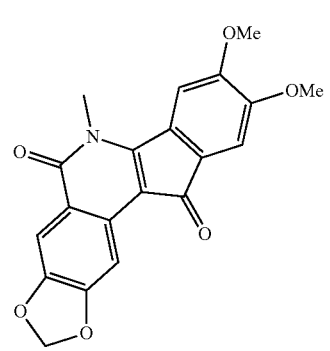 [SMILES: COc1cc2c(cc1OC)-c1c(c3cc4c(cc3c(=O)n1C)OCO4)C2=O]
(22) 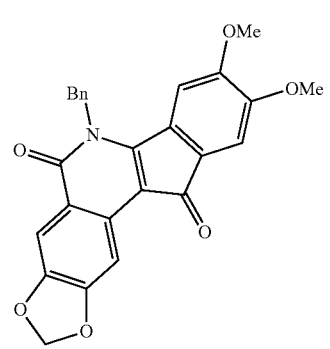 [SMILES: COc1cc2c(cc1OC)-c1c(c3cc4c(cc3c(=O)n1Cc1ccccc1)OCO4)C2=O]

(23) 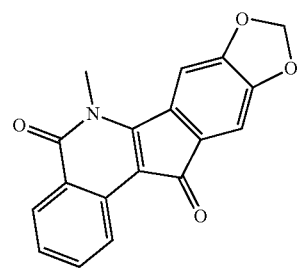
(24) 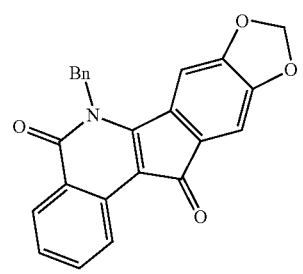
(25) 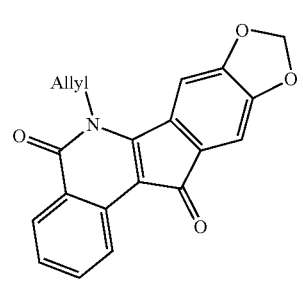
(26) 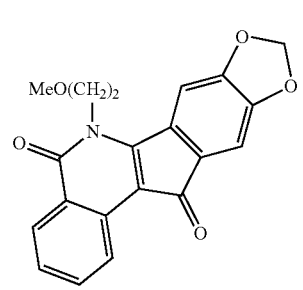
(27) 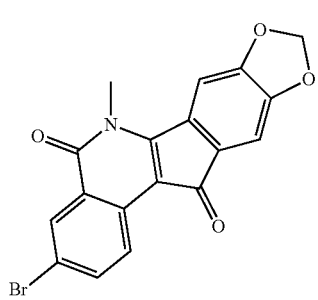
(28) 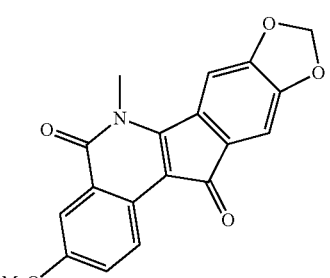
(29) 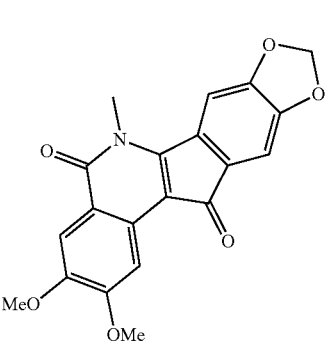
(30) 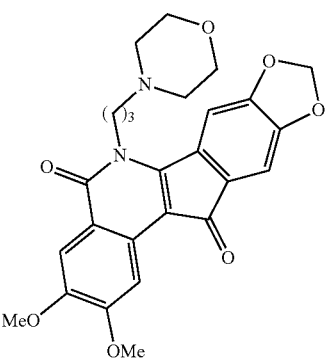
(31) 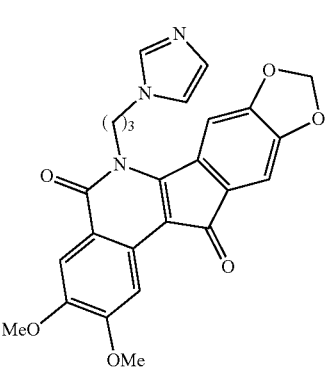
(34) 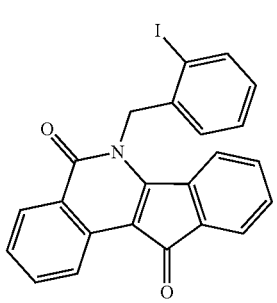 [SMILES: O=C1c2ccccc2-c2c1c1ccccc1c(=O)n2Cc1ccccc1I]

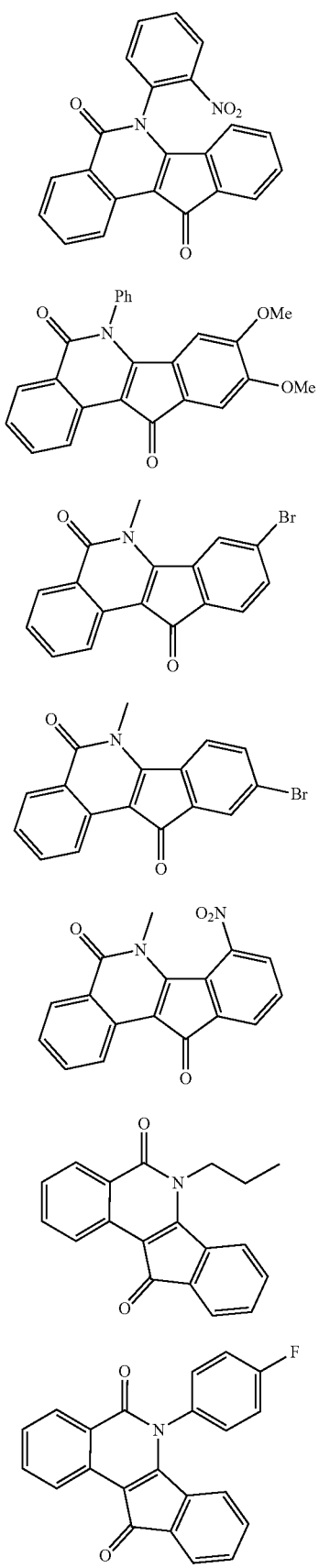
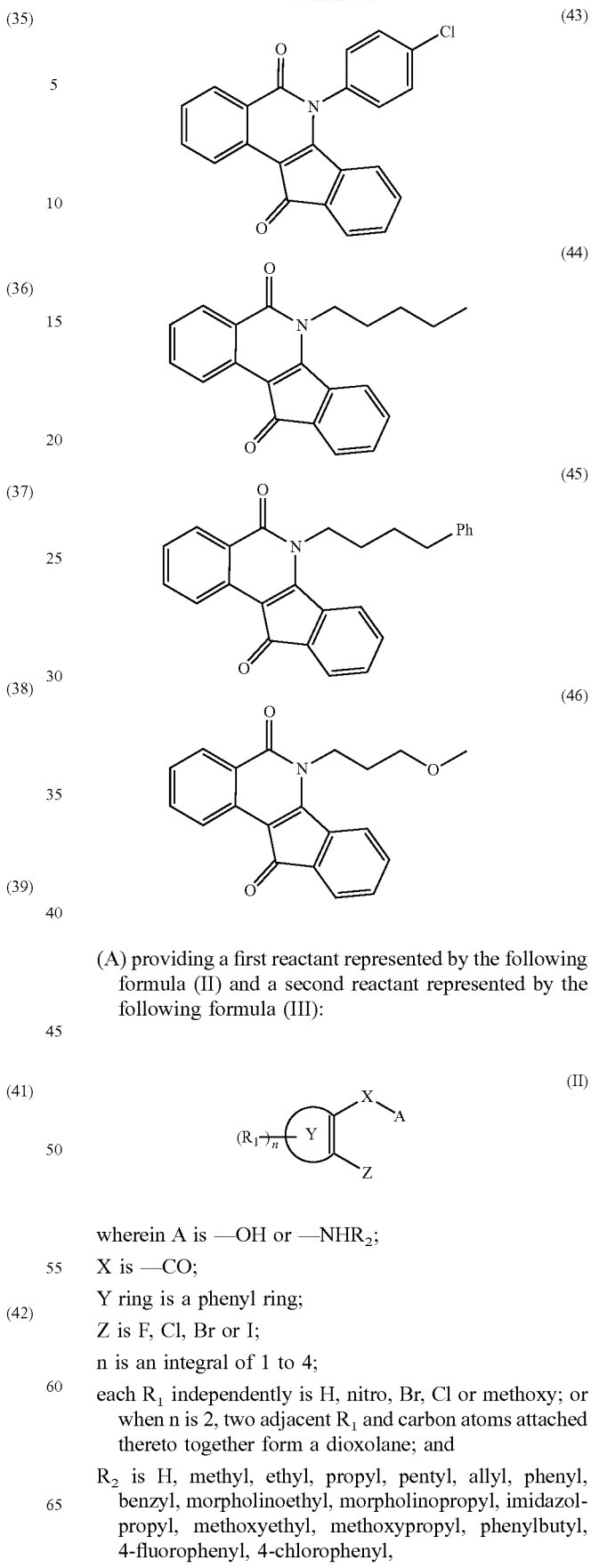

(A) providing a first reactant represented by the following formula (II) and a second reactant represented by the following formula (III):

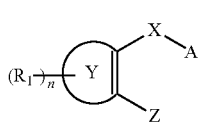

wherein A is —OH or —NHR$_2$;
X is —CO;
Y ring is a phenyl ring;
Z is F, Cl, Br or I;
n is an integral of 1 to 4;
each R$_1$ independently is H, nitro, Br, Cl or methoxy; or when n is 2, two adjacent R$_1$ and carbon atoms attached thereto together form a dioxolane; and
R$_2$ is H, methyl, ethyl, propyl, pentyl, allyl, phenyl, benzyl, morpholinoethyl, morpholinopropyl, imidazolpropyl, methoxyethyl, methoxypropyl, phenylbutyl, 4-fluorophenyl, 4-chlorophenyl,

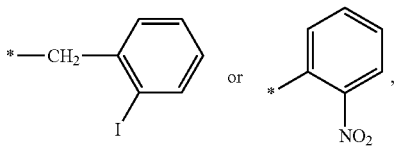 [SMILES: *Cc1ccccc1I ; *c1ccccc1[N+](=O)[O-]]

wherein * is a bonding position,

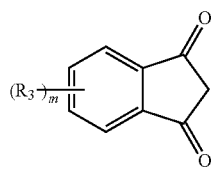
(III)

wherein m is an integral of 1 to 4; and each $R_3$ independently is H, Br, nitro or methoxy; or when m is 2, two adjacent $R_3$ and carbon atoms attached thereto together form a dioxolane; and (B) reacting the first reactant represented by the formula (II) and the second reactant represented by the formula (III) in a solvent with a catalyst and adding $R_2NH_2$ therein in the case where A is —OH, to obtain the indenoisoquinoline derivatives represented by one of the formulas (1) to (31), (34) to (39) and (41) to (46), wherein the catalyst comprises $Cu^+$ or $Cu^{2+}$.

2. The method of claim 1, wherein the solvent is water, MeCN, DMF, DMSO, dioxane, toluene, or a combination thereof.

3. The method of claim 1, wherein the catalyst is selected from the group consisting of CuI, $CuSO_4$, CuCl, $CuCl_2$, and a hydrate thereof.

4. The method of claim 1, wherein an alkali is further added in the step (B).

5. The method of claim 4, wherein the alkali is selected from the group consisting of $K_2CO_3$, $Na_2CO_3$, $Cs_2CO_3$, LiOH, NaOH, KOH, CsOH, $Li_3PO_4$, $Na_3PO_4$, $K_3PO_4$ and $Cs_3PO_4$.

6. The method of claim 1, wherein Z in the formula (II) is I.

7. The method of claim 1, wherein the formula (II) is one of the following formulas (II-4) to (II-6):

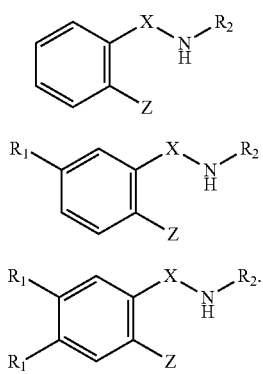

8. The method of claim 1, wherein the formula (III) is one of the following formulas (III-1) to (III-4):

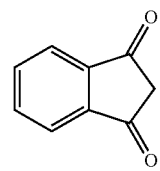
(III-1)

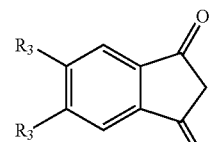
(III-2)

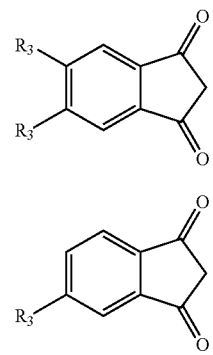
(III-3)

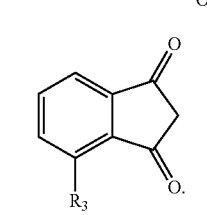
(III-4)

9. The method of claim 1, wherein the step (B) comprises the following steps in the case where A is —OH:

(B1) reacting the first reactant represented by the formula (II) and the second reactant represented by the formula (III) in the solvent with the catalyst to obtain an intermediate represented by the following formula (IV), wherein the catalyst comprises $Cu^+$ or $Cu^{2+}$:

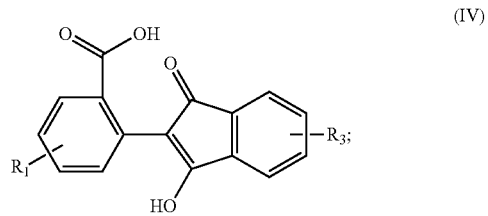
(IV)

(B2) reacting the intermediate represented by the formula (IV) with $R_2NH_2$ to obtain the indenoisoquinoline derivatives represented by one of the formulas (1) to (31), (34) to (39) and (41) to (46).

10. The method of claim 9, wherein the catalyst is selected from the group consisting of CuI, $CuSO_4$, CuCl, $CuCl_2$, and a hydrate thereof.

11. The method of claim 9, wherein an alkali is further added in the step (B1).

12. The method of claim 11, wherein the alkali is selected from the group consisting of $K_2CO_3$, $Na_2CO_3$, $Cs_2CO_3$, LiOH, NaOH, KOH, CsOH, $Li_3PO_4$, $Na_3PO_4$, $K_3PO_4$ and $Cs_3PO_4$.

13. The method of claim 9, wherein an acid is further added in the step (B2).

14. The method of claim 13, wherein the acid is camphorsulfonic acid.

* * * * *